United States Patent
Feng et al.

(10) Patent No.: US 12,329,562 B2
(45) Date of Patent: Jun. 17, 2025

(54) METHODS AND SYSTEMS FOR DETERMINING PARAMETERS RELATED TO MEDICAL OPERATIONS

(71) Applicant: SHANGHAI UNITED IMAGING HEALTHCARE CO., LTD., Shanghai (CN)

(72) Inventors: Juan Feng, Shanghai (CN); Yecheng Han, Shanghai (CN); Wei Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 337 days.

(21) Appl. No.: 18/157,796

(22) Filed: Jan. 20, 2023

(65) Prior Publication Data

US 2023/0148986 A1    May 18, 2023

Related U.S. Application Data

(63) Continuation of application No. PCT/CN2021/109902, filed on Jul. 30, 2021.

(30) Foreign Application Priority Data

Jul. 30, 2020   (CN) .......................... 202010751784.7
Aug. 7, 2020   (CN) .......................... 202010786489.5

(51) Int. Cl.
  *A61B 6/00*   (2024.01)
  *A61B 6/46*   (2024.01)

(52) U.S. Cl.
  CPC .............. *A61B 6/545* (2013.01); *A61B 6/463* (2013.01); *A61B 6/488* (2013.01); *A61B 6/542* (2013.01)

(58) Field of Classification Search
  CPC ........ G16H 30/40; G16H 30/20; G16H 30/00; G16H 50/00; G16H 50/20; G16H 70/00;
  (Continued)

(56) References Cited

U.S. PATENT DOCUMENTS

2013/0342851 A1   12/2013   Dresel et al.
2015/0012466 A1   1/2015   Sapiro et al.
(Continued)

FOREIGN PATENT DOCUMENTS

CN   102961154 A   3/2013
CN   103654809 A   3/2014
(Continued)

OTHER PUBLICATIONS

The Extended European Search Report in European Application No. 21849927.5 mailed on Jul. 20, 2023, 7 pages.
(Continued)

*Primary Examiner* — Don K Wong
(74) *Attorney, Agent, or Firm* — METIS IP LLC

(57) ABSTRACT

The embodiments of the present disclosure provides a method for determining parameters related to a medical operation. The method includes obtaining optical image information of a target object, determining target part information of the target object, and determining the parameters related to the medical operation at least based on the optical image information and the target part information.

20 Claims, 7 Drawing Sheets

(58) Field of Classification Search
CPC .................. G16H 70/20; G16H 40/60; G06T 2207/20081; G06T 7/30; A61B 6/032; A61B 6/42; A61B 6/545; A61B 6/548; A61B 5/1079; A61B 5/1128; A61B 90/361; A61B 2576/00; A61B 5/0013; A61B 34/10; A61B 2034/101; A61B 2034/107; A61B 2034/108
See application file for complete search history.

(56) References Cited

U.S. PATENT DOCUMENTS

| | | |
|---|---|---|
| 2017/0112460 A1 | 4/2017 | Merckx |
| 2018/0296177 A1 | 10/2018 | Chang et al. |
| 2018/0360408 A1 | 12/2018 | Quan |
| 2018/0368921 A1 | 12/2018 | Jeszenszky et al. |
| 2019/0243934 A1 | 8/2019 | Mak et al. |
| 2019/0261931 A1 | 8/2019 | Ross |
| 2020/0126272 A1 | 4/2020 | Baer-Beck et al. |
| 2020/0138395 A1 | 5/2020 | Tsuchiya et al. |
| 2020/0303049 A1 | 9/2020 | Zhang et al. |

FOREIGN PATENT DOCUMENTS

| | | | |
|---|---|---|---|
| CN | 107742536 A | | 2/2018 |
| CN | 107789001 A | | 3/2018 |
| CN | 107992817 A | | 5/2018 |
| CN | 108670280 A | | 10/2018 |
| CN | 109730704 A | | 5/2019 |
| CN | 109745061 A | | 5/2019 |
| CN | 110507337 A | | 11/2019 |
| CN | 111407298 A | | 7/2020 |
| CN | 111870268 A | | 11/2020 |
| CN | 112053346 A | | 12/2020 |
| CN | 112716509 A | | 4/2021 |
| CN | 113412501 A | * 9/2021 | ............ G06F 3/017 |

OTHER PUBLICATIONS

International Search Report in PCT/CN2021/109902 mailed on Nov. 3, 2021, 8 pages.
Written Opinion in PCT/CN2021/109902 mailed on Nov. 3, 2021, 12 pages.
Tang, Yansong et al., Deep Progressive Reinforcement Learning for Skeleton-based Action Recognition, CVPR, 5323-5332, 2018.
Nan, Jiang et al., Feature Hourglass Network for Skeleton Detection, CVPR, 2019, 5 pages.
Rucha Damle et al., Human Body Skeleton Detection And Tracking, International Journal of Technical Research and Applications, 3(6): 222-225, 2015.
Liu, Chang et al., Linear Span Network for Object Skeleton Detection, ECCV, Jan. 16, 2018.
Rashmi Raghavenda Patil et al., Pose Estimation For Skeleton Detection, International Journal of Engineering Applied Sciences and Technology, 4(4): 192-196, 2019.
Satish Prabhu et al., Real Time Skeleton Tracking based Human Recognition System using Kinect and Arduino, International Journal of Computer Applications, 6 pages.
Tang, Zihui, Introduction to Medical artificial intelligence, Shanghai Science and Technology Press, 2020, 6 pages.

* cited by examiner

METHODS AND SYSTEMS FOR DETERMINING PARAMETERS RELATED TO MEDICAL OPERATIONS

CROSS-REFERENCE TO RELATED APPLICATIONS

This application is a Continuation of International Application No. PCT/CN2021/109902 filed on Jul. 30, 2021, which claims priority to Chinese Patent Application No. 202010751784.7 filed on Jul. 30, 2020, and Chinese Patent Application No. 202010786489.5 filed on Aug. 7, 2020, the entire contents of each of which are incorporated herein by reference.

TECHNICAL FIELD

The present disclosure relates to parameter determination methods, and in particular to methods and systems for determining parameters related to medical operations.

BACKGROUND

Radiation devices (e.g., a DR device, a CT device, an X-ray machine, a linear accelerator, a C-arm machine, etc.) photograph and/or treat patients by emitting radiations (e.g., X-rays, p-rays, y-rays, etc.). When a radiation device emits radiations, a corresponding opening is set through a beam limiter, and the radiations pass through the opening to irradiate the human body. If a region irradiated on the human body through the opening of the beam limiter does not match a region to be irradiated on the human body, there would be a problem of receiving unnecessary radiations, and those unnecessary radiations may cause harm to the human body. Therefore, it is desirable to provide a method for determining information of a target position of a beam limiting device, thereby improving a matching degree between the opening of the beam limiter and the region to be irradiated on the human body.

SUMMARY

The present disclosure provides a method for determining parameters related to a medical operation. The method includes obtaining optical image information of a target object; determining target part information of the target object; and determining the parameters related to the medical operation at least based on the optical image information and the target part information.

In some embodiments, the determining the target part information of the target object may include obtaining the target part information of the target object.

In some embodiments, the determining the target part information of the target object may include determining the target part information of the target object by processing the optical image information.

In some embodiments, the parameters related to the medical operation may include information of a position to be irradiated on the target object and/or information of a target position of a beam limiting device. The determining the parameters related to the medical operation at least based on the optical image information and the target part information may include determining the information of the position to be irradiated on the target object and/or the information of the target position of the beam limiting device at least based on the optical image information and the target part information.

In some embodiments, the obtaining the target part information of the target object may include obtaining a medical image of the target part of the target object. The determining the information of the position to be irradiated on the target object and/or the information of the target position of the beam limiting device at least based on the optical image information and the target part information may include: determining the information of the position to be irradiated on the target object and/or the information of the target position of the beam limiting device at least based on the optical image information and the medical image.

In some embodiments, the obtaining the target part information of the target object may further include obtaining protocol information related to the target object. The protocol information at least includes the target part information of the target object. The determining the information of the position to be irradiated on the target object and/or the information of the target position of the beam limiting device at least based on the optical image information and the target part information may include determining the information of the position to be irradiated on the target object and/or the information of the target position of the beam limiting device at least based on the optical image information and the protocol information.

In some embodiments, the obtaining the target part information of the target object may further include obtaining label information of the medical image corresponding to the target object.

In some embodiments, the method may further include obtaining information of an initial position of the beam limiting device. In response to determining the information of the position to be irradiated on the target object based on the optical image information and the target part information, the method may further include determining the information of the target position of the beam limiting device based on the information of the position to be irradiated and the information of the initial position.

In some embodiments, the determining the information of the position to be irradiated on the target object based on the optical image information and the target part information may include determining the information of the position to be irradiated by inputting the optical image information and the target part information into a first machine learning model.

In some embodiments, the first machine learning model may be obtained by the following operations: obtaining an initial machine learning model; obtaining initial sample training data, the initial sample training data including historical optical images of historical target objects and historical medical images of one or more target parts of the historical target objects; determining label information of the historical optical images based on fusion result information of the historical optical images and the historical medical images, the label information including position information of the target parts in the historical optical images; and inputting the historical optical images and the historical medical images as input data and the label information as output data into the initial machine learning model for training.

In some embodiments, the determining the information of the target position of the beam limiting device based on the optical image information and the target part information may include determining the information of the target position of the beam limiting device by inputting the optical image information and the target part information into a second machine learning model.

In some embodiments, the second machine learning model may be obtained by the following operations: obtaining an initial machine learning model; obtaining initial sample training data, the initial sample training data including historical optical images of historical target objects and historical medical images of one or more target parts of the historical target objects; determining information of historical target positions of the beam limiting device based on fusion result information of the historical optical images and the historical medical images; and inputting the historical optical images and the historical medical images as input data and the information of the historical target positions of the beam limiting device as output data into the initial machine learning model for training.

In some embodiments, a movement of the beam limiting device may be controlled based on the information of the target position of the beam limiting device.

In some embodiments, in response to that the information of the target position is greater than a preset threshold range, a prompt message may be sent.

In some embodiments, the information of the position to be irradiated may include at least two sub-regions to be irradiated. The information of the target position of the beam limiting device may include information of at least two sub-target positions corresponding to the at least two sub-regions to be irradiated.

In some embodiments, the protocol information related to the target object may include at least two sub-target parts, accordingly, the at least two sub-regions to be irradiated may be determined based on the at least two sub-target parts in the protocol information.

In some embodiments, the at least two sub-regions to be irradiated may be determined by a preset algorithm, accordingly, the information of the at least two sub-target positions of the beam limiting device may be determined based on the at least two sub-regions to be irradiated.

In some embodiments, the beam limiting device may include a multi-leaf collimator.

In some embodiments, the parameters related to the medical operation may include the label information of the medical image corresponding to the target object. The target part information may include orientation information of the target part. The determining the parameters related to the medical operation at least based on the optical image information and the target part information may include determining the label information of the medical image based on the orientation information of the target part.

In some embodiments, the method may further include labelling the medical image of the target object based on the orientation information of the target part.

In some embodiments, the method may include obtaining the medical image of the target object and labelling the label information in the medical image.

In some embodiments, the labelling the medical image of the target object based on the orientation information may include determining the protocol information based on the orientation information and labelling the medical image of the target object based on the protocol information.

In some embodiments, the orientation information may include at least one of a left-right orientation, a front-rear orientation, or an up-down orientation of the target part relative to the target object.

In some embodiments, the optical image information of the target object may include a still image or a video image.

In some embodiments, in response to that the orientation information of the target part is obtained by processing the optical image information, the optical image information may be processed through a preset algorithm, the preset algorithm including a machine learning model, accordingly, the determining the orientation information of the target part of the target object by processing the optical image information may include inputting the optical image information into the machine learning model and determining the orientation information of the target part based on output data of the machine learning model.

In some embodiments, the optical image information may be obtained by a camera. The medical image may be one of or a fusion image of at least two of an MRI image, an XR image, a PET image, a SPECT image, a CT image, or an ultrasound image.

In some embodiments, the method may further include automatically adjusting a ray source of a medical imaging device based on the optical image information of the target part, so that the target part may be in a ray path of the ray source.

In some embodiments, the labelling the medical image of the target object based on the orientation information may include color labelling, text labelling, or graphic labelling.

In some embodiments, the method may further include manually adjusting a label of a labelled medical image.

The present disclosure provides a system for determining parameters related to a medical operation. The system may include an optical image information obtaining module, a target part information determination module, and a medical operation parameter determination module. The optical image information obtaining module may be configured to obtain optical image information of a target object. The target part information determination module may be configured to determine target part information of the target object. The medical operation parameter determination module may be configured to determine the parameters related to the medical operation at least based on the optical image information and the target part information.

In some embodiments, the target part information determination module may be further configured to obtain the target part information of the target object.

In some embodiments, the target part information determination module may be further configured to determine the target part information of the target object by processing the optical image information.

In some embodiments, the parameters related to the medical operation may include information of a position to be irradiated on the target object and/or information of a target position of a beam limiting device. The medical operation parameter determination module may be further configured to determine the information of the position to be irradiated on the target object and/or the information of the target position of the beam limiting device at least based on the optical image information and the target part information.

In some embodiments, the obtaining the target part information of the target object may include obtaining a medical image of a target part of the target object. The determining the information of the position to be irradiated on the target object and/or the information of the target position of the beam limiting device at least based on the optical image information and the target part information may include determining the information of the position to be irradiated on the target object and/or the information of the target position of the beam limiting device at least based on the optical image information and the medical image.

In some embodiments, the obtaining the target part information of the target object may further include obtaining protocol information related to the target object. The protocol information at least includes the target part information of the target object. The determining the information of the position to be irradiated on the target object and/or the information of the target position of the beam limiting device at least based on the optical image information and the target part information may include determining the information of the position to be irradiated on the target object and/or the information of the target position of the beam limiting device at least based on the optical image information and the protocol information.

In some embodiments, the obtaining the target part information of the target object may further include obtaining label information of the medical image corresponding to the target object.

In some embodiments, the system may further include obtaining information of an initial position of the beam limiting device. In response to determining the information of the position to be irradiated on the target object based on the optical image information and the target part information, the method may further include determining the information of the target position of the beam limiting device based on the information of the position to be irradiated and the information of the initial position.

In some embodiments, the determining the information of the position to be irradiated on the target object based on the optical image information and the target part information may include determining the information of the position to be irradiated by inputting the optical image information and the target part information into a first machine learning model.

In some embodiments, the first machine learning model may be obtained by the following operations: obtaining an initial machine learning model; obtaining initial sample training data, the initial sample training data including historical optical images of historical target objects and historical medical images of one or more target parts of the historical target objects; determining label information of the historical optical images based on fusion result information of the historical optical images and the historical medical images, the label information may include position information of the target parts in the historical optical images; and inputting the historical optical images and the historical medical images as input data and the label information as output data into the initial machine learning model for training.

In some embodiments, the determining the information of the target position of the beam limiting device based on the optical image information and the target part information may include determining the information of the target position of the beam limiting device by inputting the optical image information and the target part information into a second machine learning model.

In some embodiments, the second machine learning model may be obtained by the following operations: obtaining an initial machine learning model; obtaining initial sample training data, the initial sample training data including historical optical images of historical target objects and historical medical images of one or more target parts of the historical target objects; determining information of historical target positions of the beam limiting device based on fusion result information of the historical optical images and the historical medical images; and inputting historical optical images and the historical medical images as input data and the information of the historical target positions of the beam limiting device as output data into the initial machine learning model for training.

In some embodiments, a movement of the beam limiting device may be controlled based on the information of the target position of the beam limiting device.

In some embodiments, in response to that the information of the target position is greater than a preset threshold range, a prompt message may be sent.

In some embodiments, the information of the position to be irradiated may include at least two sub-regions to be irradiated. The information of the target position of the beam limiting device may include information of at least two sub-target positions corresponding to the at least two sub-regions to be irradiated.

In some embodiments, the protocol information related to the target object may include at least two sub-target parts, accordingly, the at least two sub-regions to be irradiated may be determined based on the at least two sub-target parts in the protocol information.

In some embodiments, the at least two sub-regions to be irradiated may be determined by a preset algorithm, accordingly, the information of the at least two sub-target positions of the beam limiting device may be determined based on the at least two sub-regions to be irradiated.

In some embodiments, the beam limiting device may include a multi-leaf collimator.

In some embodiments, the parameters related to the medical operation may include the label information of the medical image corresponding to the target object. The target part information may include orientation information of the target part. The medical operation parameter determination module may be further configured to: determine the label information of the medical image based on the orientation information of the target part.

In some embodiments, the system may further include labelling the medical image of the target object based on the orientation information of the target part.

In some embodiments, the medical image of the target object may be obtained, and the label information may be labelled in the medical image.

In some embodiments, the labelling the medical image of the target object based on the orientation information may include determining the protocol information based on the orientation information and labelling the medical image of the target object based on the protocol information.

In some embodiments, the orientation information may include at least one of a left-right orientation, a front-rear orientation, of an up-down orientation of the target part relative to the target object.

In some embodiments, the optical image information of the target object may include a still image or a video image.

In some embodiments, in response to that the orientation information of the target part is obtained by processing the optical image information, the optical image information may be processed through a preset algorithm, the preset algorithm including a machine learning model, accordingly, the determining the orientation information of the target part of the target object by the processing the optical image information may include inputting the optical image information into the machine learning model and determining the orientation information of the target part based on output data of the machine learning model.

In some embodiments, the optical image information may be obtained by a camera. The medical image may be one of or a fusion image of at least two of an MRI image, an XR image, a PET image, a SPECT image, a CT image, or an ultrasound image.

In some embodiments, the system may further include automatically adjusting a ray source of a medical imaging device based on the optical image information of the target part, so that the target part may be in a ray path of the ray source.

In some embodiments, the labelling the medical image of the target object based on the orientation information may include color labelling, text labelling, or graphic labelling.

In some embodiments, the system may further include manually adjusting a label of a labelled medical image.

The present disclosure provides a system for determining information of a target position of a beam limiting device. The system includes an optical image information obtaining module, a target part information obtaining module, and a determination module. The optical image information obtaining module is configured to obtain optical image information of a target object. The target part information obtaining module is configured to obtain target part information of the target object. The determination module is configured to determine information of a position to be irradiated on the target object and/or the information of the target position of the beam limiting device at least based on the optical image information and the target part information.

The present disclosure provides a device for determining an operating position, comprising a processor. The processor is configured to execute any method for determining the information of the target position of the beam limiting device.

The present disclosure provides a computer-readable storage medium storing computer instructions. After reading the computer instructions in the storage medium, a computer may execute any method for determining the information of the target position of the beam limiting device.

The present disclosure provides a system for labelling an orientation of a target part. The system includes an image information obtaining module, an orientation information determination module, and an orientation information labelling module. The orientation information determination module is configured to obtain image information of the target part of a target object. The orientation information determination module is configured to determine orientation information of the target part of the target object by processing the image information. The orientation information labelling module is configured to label a medical image of the target object based on the orientation information.

In some embodiments, the system may further include a camera configured to obtain the image information. The medical image may be one of or a fusion image of at least two of an MRI image, an XR image, a PET image, a SPECT image, a CT image, or an ultrasound image.

In some embodiments, a device for labelling an orientation of a target part may include a processor. The processor may be configured to execute computer instructions to implement any method for labelling an orientation of a target part.

The present disclosure provides a system for labelling an orientation of a target part. The system may include a camera device, a medical imaging device, and an information processing device. The camera device is configured to obtain image information of the target part of a target object. The medical imaging device is configured to obtain a medical image of the target object. The information processing device is configured to determine orientation information of the target part of the target object by processing the image information and label the orientation information in the medical image.

In some embodiments, the camera device may be relatively fixedly or movably arranged on the medical imaging device.

In some embodiments, the camera device may be a camera.

BRIEF DESCRIPTION OF THE DRAWINGS

The present disclosure is further illustrated in terms of exemplary embodiments. These exemplary embodiments are described in detail with reference to the drawings. These embodiments are non-limiting. In these embodiments, the same number indicates the same structure, wherein.

DETAILED DESCRIPTION

Figure 1:
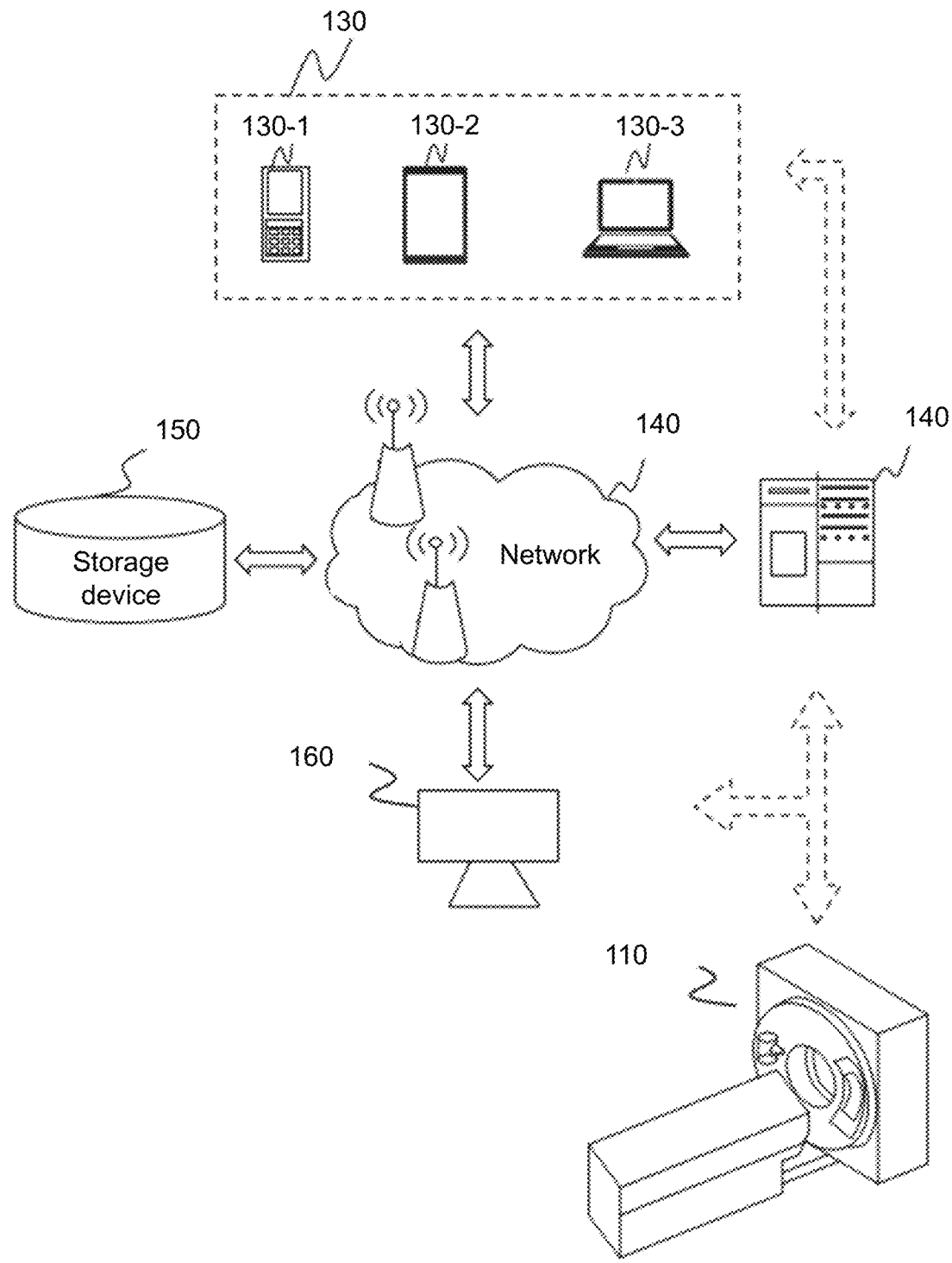
FIG. 1 is a schematic diagram illustrating an application scenario of a system for determining information of a target position of a beam limiting device according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. It should be understood that the exemplary embodiments are provided merely for better comprehension and application of the present disclosure by those skilled in the art, and are not intended to limit the scope of the present disclosure. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

In many medical operation scenarios, the parameters related to the medical operations need to adjust based on different characteristics of different patients. For example, in a medical operation scenario of radiotherapy, it is necessary to determine a position of a part to be irradiated according to sign information (e.g., a height, a body width, or a body thickness) of different patients, and then to adjust a position of an opening of a beam limiting device, so that the position of the opening of the beam limiting device can be matched as much as possible the position of the part to be irradiated of the patient. As another example, after a patient takes a medical image, it is necessary to label the medical image to inform a doctor or the patient of the photographing part corresponding to the medical image. In order to ensure the accuracy of the label information and the photographing part, it is necessary to label medical images based on the current photographing parts of different patients and orientations of the photographing parts.

In order to ensure the accuracy and efficiency of the medical operation, in one or more embodiments of the present disclosure, a visual recognition may be implemented through a camera device, and the parameters related to the medical operation may be generated based on the recognition result or other information. In some embodiments, the optical image information of the target object may be obtained first by the camera device, then the target part information of the target object may be determined, and finally the parameters related to the medical operation may be determined at least based on the optical image information and the target part information.

In some embodiments, the parameters related to the medical operation may include information of a position to be irradiated on the target object and/or information of a target position of a beam limiting device.

In some embodiments, the parameters related to the medical operation may include label information of a medical image corresponding to the target object.

One or more embodiments of the present disclosure relate to a method and a system for determining parameters related to a medical operation. When the parameters related to the medical operation include information of a position to be irradiated on a target object and/or information of a target position of a beam limiting device, the method and the system for determining the parameters related to the medical operation in the one or more embodiments of the present disclosure may also be referred to as a method and a system for determining the information of the target position of the beam limiting device. The method for determining the information of the target position of the beam limiting device may be applied to a beam limiter of a radiation device (e.g., a DR device, a CT device, etc.). Before each irradiation of the radiation device, the method may include automatically determining the information of the target position of the beam limiting device at least based on optical image information and target part (e.g., an irradiated organ in a medical task) information of a target object (e.g., a human body or other experimental bodies) that are automatically obtained, so that a region where rays pass through the target position of the beam limiting device and irradiate the target object may match as much as possible with a region to be irradiated, thereby avoiding unnecessary radiation dose damage to the target object while ensuring the imaging/treatment quality. The above method may be especially suitable for use when children are exposed to radiation, so as to realize protection of children from radiation damage.

When the parameters related to the medical operation include label information of a medical image corresponding to the target object, the method and the system for determining the parameters related to the medical operation in the one or more embodiments of the present disclosure may also be referred to as a method and a method for labelling an orientation of a target part. In some embodiments, it is necessary to manually recognize a photographing part in the medical image and manually label the photographing part in the medical image. In some embodiments, during the actual photographing process, a doctor may select a photographing protocol based on a known photographing part, and a medical imaging device may label orientation information based on the selected protocol. During the above process, errors in judgment, calibration, or protocol selection may occur, which may have a certain impact on the diagnosis result and subsequent treatment. The method for labelling the target part provided in some embodiments of the present disclosure may include obtaining image information of the target object, processing the image information based on a preset algorithm, determining the orientation information of the target part of the target object, and labeling the medical image of the target part based on the orientation information.

The system for determining the parameters related to the medical operation provided in the embodiments of the present disclosure would be described in detail below with reference to the accompanying drawings.

FIG. 1 is a schematic diagram illustrating an application scenario of a system for determining parameters related to a medical operation according to some embodiments of the present disclosure.

As shown in FIG. 1, the system 100 for determining the parameters related to the medical operation may include a medical imaging device 110, a network 120, a processing device 140, a storage device 150, and a camera device 160. In some embodiments, the system 100 may further include at least one terminal 130. The components of the system 100 may be connected to each other through the network 120. For example, the camera device 160 and the processing device 140 may be connected or communicate through the network 120.

In some embodiments, the medical imaging device 110 may collect data on the target object to obtain a medical image of a target object or a target part of the target object. In some embodiments, the medical imaging device may include a digital radiography (DR) imaging device, a computed tomography (CT) scanner, a magnetic resonance imaging (MRI) scanner, a B-scan ultrasonography scanner, a thermal texture maps (TTM) scanning device, or a positron emission tomography (PET) scanner, etc. For example, the medical imaging device 110 may be described by taking the CT scanner as an example. For example, the system may analyze image information obtained by the camera device 160 to determine that the target part is the left knee. The target object may lie flat on a scanning bed face up, and the scanning bed may be moved to make the left knee in a scanning region for scanning to obtain a medical image of the left knee. In some embodiments, when the medical imaging device 110 is the CT device, the device may include a beam limiting device (e.g., a beam limiter) configured to limit a light-transmitting region of radiation emitted by the CT device. In some embodiments, the medical imaging device 110 may be any other radiation device. The radiation device may photograph and/or treat the target object by emitting radiation (e.g., X-rays, β-rays, γ-rays, etc.). For example, the radiation device may include, but is not limited to, a DR device, an X-ray machine, a linear accelerator, a C-arm machine, or the like. In some embodiments, the beam limiting device may include a multi-leaf collimator which may adapt to regions to be irradiated of different shapes or any irregular shapes, thereby improving the accuracy of adaptation and reducing the harm of unnecessary radiation dose to the human body.

In some embodiments, the camera device 160 may collect data on the target object to obtain optical image information of the target object or the target part of the target object. In some embodiments, the camera device 160 may be arranged on the medical imaging device 110, or may be arranged independently from the medical imaging device 110. In some embodiments, the camera device 160 may be an optical device, such as a camera or other image sensors. In some embodiments, the camera device 160 may be a non-optical device that may obtain a heat map capable of reflecting features such as a shape and a size of the target object based on collected distance data. In some embodiments, the optical image information collected by the camera device 160 may be a still image or a video image. In some embodiments, the camera device 160 may include a camera.

The network 120 may include any suitable network capable of facilitating the exchange of information and/or data for the system 100. In some embodiments, at least one component (e.g., the camera device 160, the processing device 140, the storage device 150, the medical imaging device 110, and the at least one terminal 130) of the system 100 may exchange information and/or data with at least one other component of the system 100 through the network 120. For example, the processing device 140 may obtain the optical image information of the target object or the target part of the target object from the camera device 160 through the network 120. As another example, the processing device 140 may obtain a user (e.g., a doctor) instruction from the at least one terminal 130 through the network 120. The network 120 may be or include a public network (e.g., Internet), a private network (e.g., a local area network (LAN)), a wired network, a wireless network (e.g., an 802.11 network, a Wi-Fi network), a frame relay network, a virtual private Internet (VPN), a satellite network, a telephone network, a router, a hub, a switch, a server computer, or any combination thereof. For example, the network 120 may include a wired network, a wireless network, a fiber optic network, a telecommunications network, an intranet, a wireless local area network (WLAN), a metropolitan area network (MAN), a public switched telephone network (PSTN), a Bluetooth™ network, a ZigBee™ network, a near field communication (NFC) network, or the like, or any combination thereof. In some embodiments, the network 120 may include at least one network access point. For example, the network 120 may include a wired and/or wireless network access point, such as a base station and/or internet exchange point. At least one component of the system 100 for determining the information of the target position of the beam limiting device may be connected to the network 120 through the access point to exchange data and/or information.

In some embodiments, the at least one terminal 130 may have a communication connection with at least one of the camera device 160, the medical imaging device 110, the processing device 140, or the storage device 150. For example, the at least one terminal 130 may obtain, display, and output information of a position to be irradiated on the target object and/or information of the target position of the beam limiting device from the processing device 140. As another example, the at least one terminal 130 may obtain an operation instruction of a user, and then send the operation instruction to the camera device 160 and/or the medical imaging device 110 to control the camera device 160 and/or the medical imaging device 110 (e.g., adjusting an image collection angle of view, setting working parameters of the beam limiting device, etc.). As a further example, the at least one terminal 130 may obtain an orientation analysis result of the target part from the processing device 140, or collected image information from the camera device 160. As a still further example, the at least one terminal 130 may obtain the operation instruction of the user, and then send the operation instruction to the medical imaging device 110 or the camera device 160 to control the medical imaging device 110 or the camera device 160 (e.g., adjusting the image collection angle of view, setting the working parameters of the medical imaging device, etc.).

In some embodiments, the at least one terminal 130 may include a mobile device 131, a tablet computer 132, a laptop computer 133, or the like, or any combination thereof. For example, the mobile device 131 may include a mobile phone, a personal digital assistant (PDA), a medical device, or the like, or any combination thereof. In some embodiments, the at least one terminal 130 may include an input device, an output device, or the like. The input device may include alphanumeric and other keys for inputting a control instruction to control the camera device 160 and/or the medical imaging device 110. The input device may be keyboard input, touch screen (e.g., with tactile or tactile feedback) input, voice input, gesture input, or any other similar input mechanisms. Input information received via the input device may be transmitted, e.g., via a bus, to the processing device 140 for further processing. Other types of input devices may include a cursor control device, such as a mouse, a trackball, a cursor direction key, or the like. The output device may include a display, a speaker, a printer, or any combination thereof, and may be configured to output the optical image information of the target object collected by the camera device 160 and/or a medical image collected by the medical imaging device 110. In some embodiments, the at least one terminal 130 may be a part of the processing device 140.

The processing device 140 may process data and/or instruction obtained from the camera device 160, the storage device 150, the at least one terminal 130, or other components of the system 100. For example, the processing device 140 may process the optical image information of the target object obtained by the camera device 160 to obtain body posture information of the target object. The body posture information may include, but is not limited to, height and body width information, and bone joint point information, etc., of the target object. For example, the processing device 140 may obtain the optical image information of the target object from the camera device 160 and process the optical image information of the target object to obtain orientation information of the target part of the target object. As another example, the processing device 140 may obtain a pre-stored instruction from the storage device 150, and execute the instruction to implement the method for determining the information of the target position of the beam limiting device as described hereinafter.

In some embodiments, the processing device 140 may be a single server or a server group. The server group may be centralized or distributed. In some embodiments, the processing device 140 may be local or remote. For example, the processing device 140 may access information and/or data from camera device 160, the storage device 150, and/or the at least one terminal 130 through the network 120. As another example, the processing device 140 may be directly connected to the camera device 160, the at least one terminal 130, and/or the storage device 150 to access the information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or any combination thereof.

In some embodiments, the medical imaging device 110 may operate based on the information of the position to be irradiated on the target object and/or the information of the target position of the beam limiting device obtained by the processing device 140. For example, the medical imaging device 110 may set a position and an opening size of the beam limiting device size based on the information of the target position of the beam limiting device (e.g., the position of the beam limiting device, the opening size of the beam limiting device, etc.) obtained by the processing device 140. In some embodiments, the medical imaging device 110 may determine the information of the target position of the beam limiting device based on the information of the position to be irradiated on the target object and information of an initial position of the beam limiting device obtained by the processing device 140.

In some embodiments, the medical imaging device 110 may perform scanning based on orientation information of the target part of the target object determined by the processing device 140. For example, the medical imaging device 110 may scan the target part (e.g., the left knee) based on the orientation information of the target part (e.g., the left knee) of the target object obtained by the processing device 140 to obtain a medical image of the target part.

The storage device 150 may store data, instructions, and/or any other information. In some embodiments, the storage device 150 may store the optical image information collected by the camera device 160 and the medical image collected by the medical imaging device 110. In some embodiments, the storage device 150 may store data obtained from the camera device 160, the at least one terminal 130, and/or the processing device 140. In some embodiments, the storage device 150 may store a historical image information library of the target object. Each historical image in the historical image information library may correspond to an optical image of the target object. In some embodiments, the storage device 150 may store protocol information related to the target object. The protocol information may at least include the target part information of the target object. The processing device 140 may obtain the target part information of the target object based on the protocol information. In some embodiments, the storage device 150 may store the information of the target position of the beam limiting device. The medical imaging device 110 may obtain the pre-stored information of the target position of the beam limiting device from the storage device 150, and control movement of the beam limiting device based on the information of the target position of the beam limiting device. In some embodiments, the storage device 150 may store a preset threshold range and a prompt message. The processing device 140 may determine whether the information of the target position is greater than the preset threshold range based on the stored prompt message, the preset threshold range, and the information of the target position. In response to that the information of the target position is greater than the preset threshold range, the processing device 140 may send the prompt message.

In some embodiments, the storage device 150 may store the medical image collected by the medical imaging device 110. In some embodiments, the storage device 150 may store data obtained from the medical imaging device 110, the t least one terminal 130, and/or the processing device 140. In some embodiments, the storage device 150 may store a correspondence relationship between the target part and the orientation information. The processing device 140 may obtain the orientation information of the target part based on the correspondence relationship and the target part.

In some embodiments, the storage device 150 may store data and/or instructions that processing device 140 executes or uses to perform the exemplary method described herein. In some embodiments, the storage device 150 may include a mass memory, a removable memory, a volatile read-write memory, a read-only memory (ROM), or the like, or any combination thereof. Exemplary mass memory may include a magnetic disk, an optical disk, a solid-state disk, or the like. Exemplary removable memory may include a flash drive, a floppy disk, an optical disk, a memory card, a compact disk, a magnetic tape, or the like. Exemplary volatile read-write memory may include a random access memory (RAM). In some embodiments, the storage device 150 may be implemented on a cloud platform.

In some embodiments, the storage device 150 may be connected to the network 120 to communicate with at least one other component (e.g., the processing device 140, the at least one terminal 130) of system 100. The at least one component of the system 100 may access data or instructions stored in the storage device 150 through the network 120. In some embodiments, the storage device 150 may be a part of the processing device 140.

It should be noted that the above description is merely provided for the purposes of illustration, and not intended to limit the scope of the embodiments. For persons having ordinary skills in the art, multiple variations and modifications may be made under the teachings of the present disclosure. The features, structures, methods, and other features of the exemplary embodiments described herein may be combined in various ways to obtain additional and/or alternative exemplary embodiments. For example, the storage device 150 may be a data storage device including a cloud computing platform, such as a public cloud, a private cloud, a community cloud, a hybrid cloud, or the like. However, those variations and modifications do not depart from the scope of the present disclosure.

In some embodiments, the system for determining the parameters related to the medical operation may further include an optical image information obtaining module, a target part information determination module, and a medical operation parameter determination module. The optical image information obtaining module may be configured to obtain optical image information of a target object. The target part information determination module may be configured to determine target part information of the target object. The medical operation parameter determination module is configured to determine the parameters related to the medical operation at least based on the optical image information and the target part information.

In some embodiments, the target part information determination module may also be configured to obtain the target part information of the target object. In some embodiments, the target part information determination module may be further configured to determine the target part information of the target object by processing the optical image information. In some embodiments, in response to that the parameters related to the medical operation include information of a position to be irradiated on the target object and/or information of a target position of a beam limiting device, the medical operation parameter determination module may be further configured to determine the information of the position to be irradiated on the target object and/or the information of the target position of the beam limiting device at least based on the optical image information and the target part information. In some embodiments, in response to that the parameters related to the medical operation include label information of a medical image corresponding to the target object, and the target part information includes orientation information of a target part, the medical operation parameter determination module may be further configured to determine the label information of the medical image based on the orientation information of the target part.

Figure 2:
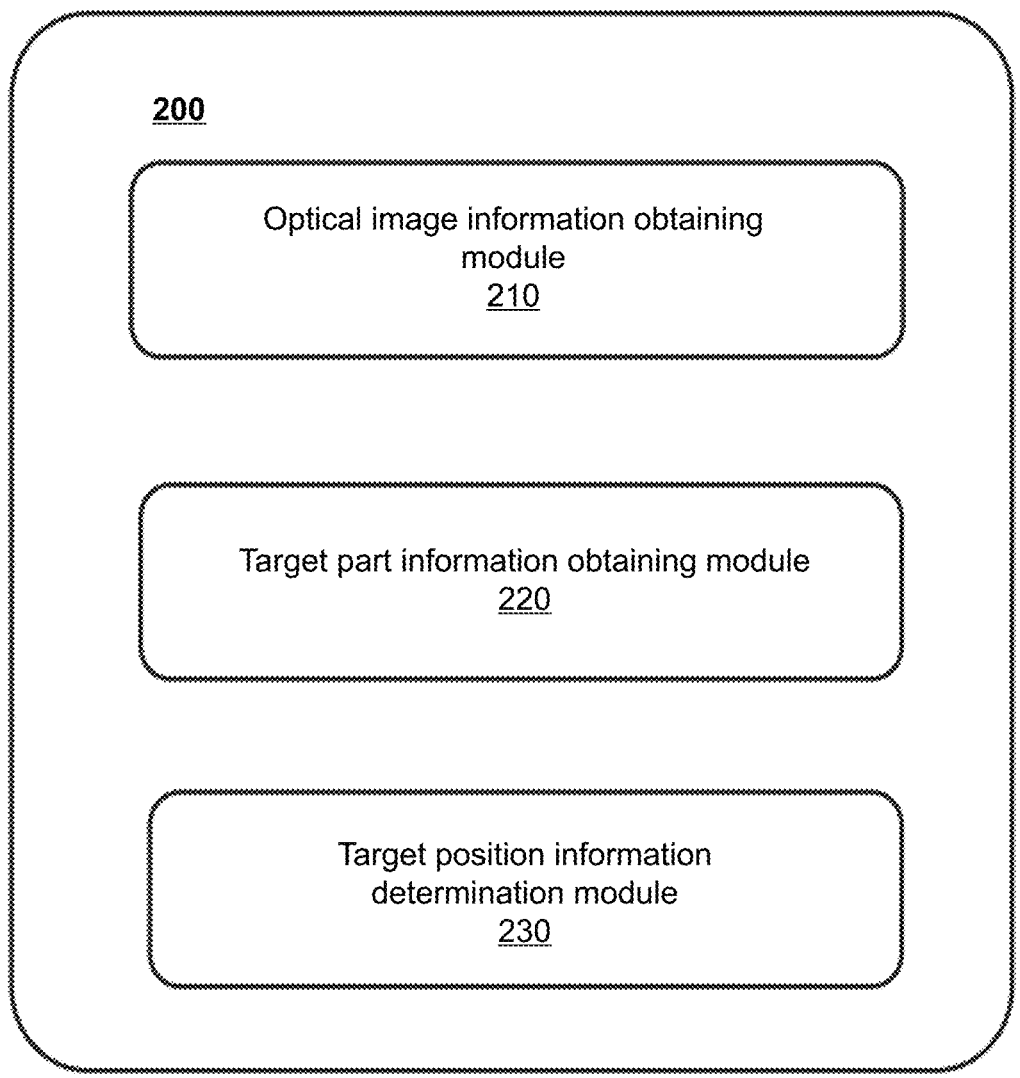
FIG. 2 is a block diagram illustrating a system for determining information of a target position of a beam limiting device according to some embodiments of the present disclosure.
Figure 3:
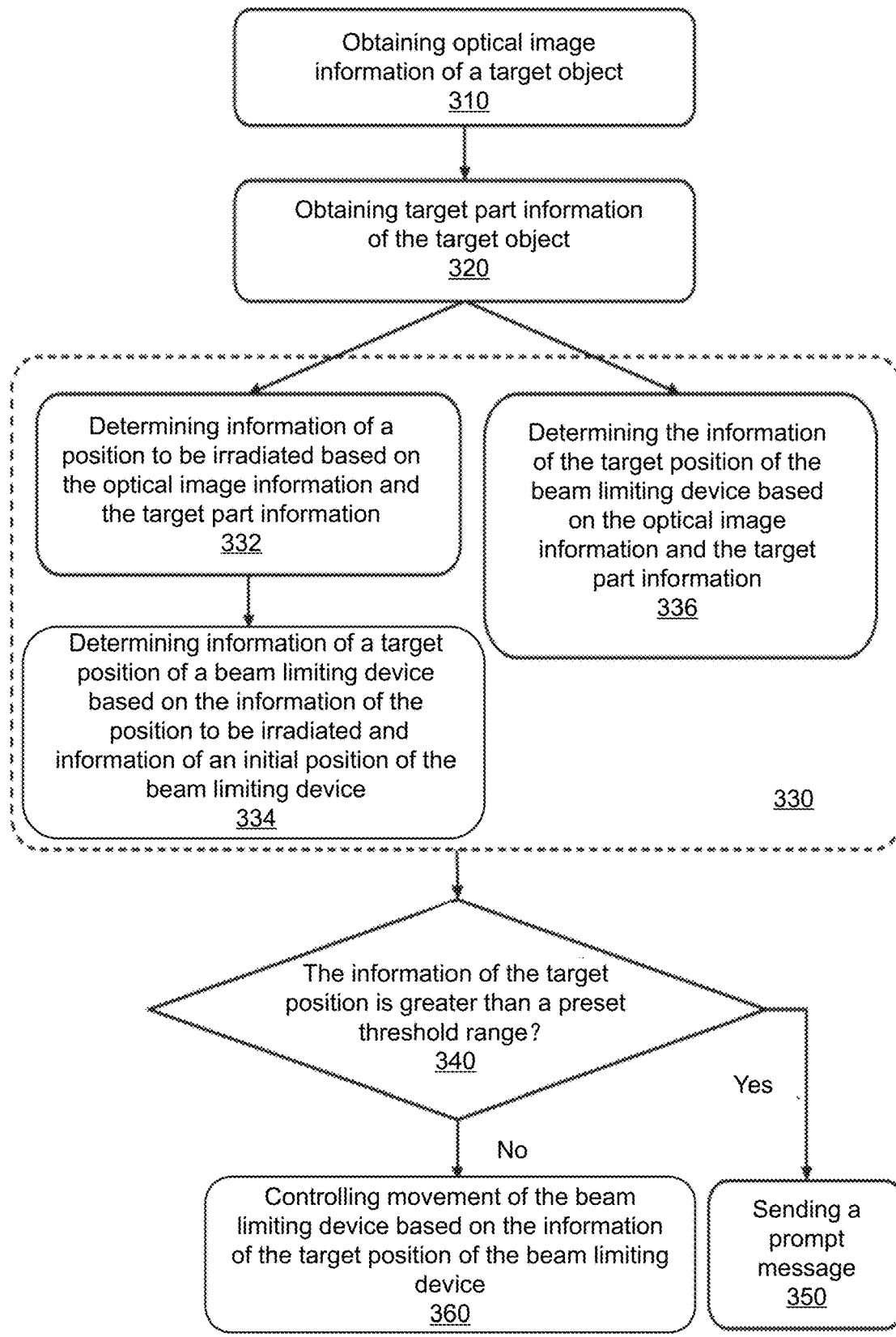
FIG. 3 is a flowchart illustrating an exemplary process for determining information of a target position of a beam limiting device according to some embodiments of the present disclosure.

The system and method for determining the parameters related to the medical operation would be exemplarily described below in combination with different scenarios. FIGS. 2-3 are exemplary descriptions of the system and method for determining the information of the target position of the beam limiting device. FIGS. 4-7 are exemplary descriptions of a system and method for labelling an orientation of a target part.

FIG. 2 is a block diagram illustrating a system 200 for determining information of a target position of a beam limiting device according to some embodiments of the present disclosure. As shown in FIG. 2, the system 200 for determining the information of the target position may include an optical image information obtaining module 210, a target part information obtaining module 220, and a target position information determination module 230. The target part information obtaining module may be included in the target part information determination module. The target position information determination module may include a module for determining parameters related to a medical operation.

The optical image information obtaining module 210 may be configured to obtain optical image information of a target object.

The target part information obtaining module 220 may be configured to obtain target part information of the target object. In some embodiments, the target part information obtaining module 220 may further be configured to obtain protocol information related to the target object. The protocol information may at least include the target part information of the target object. In some embodiments, the target part information obtaining module 220 may further be configured to obtain a medical image of a target part of the target object.

The target position information determination module 230 may be configured to determine information of a position to be irradiated on the target object and/or information of a target position of a beam limiting device at least based on the optical image information and the target part information. In some embodiments, the target position information determination module 230 may further be configured to determine the information of the position to be irradiated on the target object and/or the information of the target position of the beam limiting device at least based on the optical image information and the medical image. In some embodiments, the target position information determination module 230 may further be configured to determine the information of the position to be irradiated on the target object and/or the information of the target position of the beam limiting device at least based on the optical image information and the protocol information. In some embodiments, the target position information determination module 230 may be configured to determine the information of the target position of the beam limiting device by inputting the optical image information and the target part information into a second machine learning model. In some embodiments, the target position information determination module 230 may be configured to determine the information of the target position of the beam limiting device based on the information of the position to be irradiated and information of an initial position. In some embodiments, the target position information determination module 230 may be configured to determine the information of the position to be irradiated by inputting the optical image information and the target part information into a first machine learning model.

In some embodiments, the system 200 for determining the information of the target position may further include a control module. The control module may be configured to determine whether the information of the target position is greater than a preset threshold range. In response to that the information of the target position is less than or equal to the preset threshold range, the control module may be configured to control movement of the beam limiting device based on the information of the target position of the beam limiting device. In response to that the information of the target position is greater than the preset threshold range, the control module may be configured to send a prompt message.

In some embodiments, the system 200 for determining the information of the target position may further include an initial position obtaining module configured to obtain information of an initial position of the beam limiting device.

In some embodiments, the system 200 for determining the information of the target position may further include a training module configured to obtain the first machine learning model by the following operations including obtaining an initial machine learning model; obtaining initial sample training data, the initial sample training data including historical optical images of historical target objects and historical medical images of one or more target parts of the historical target objects; determining label information of the historical optical images based on fusion result information of the historical optical images and the historical medical images, the label information including position information of target parts in the historical optical images; and inputting the historical optical image and the historical medical image as input data and the label information as output data or a reference standard into the initial machine learning model for training.

In some embodiments, the training module may be further configured to obtain the second machine learning model by the following operations including obtaining an initial machine learning model; obtaining initial sample training data, the initial sample training data including historical optical images of historical target objects and historical medical images of one or more target parts of the historical target objects; determining information of historical target positions of the beam limiting device based on fusion result information of the historical optical images and the historical medical images; and inputting the historical optical image and the historical medical image as input data and the information of the historical target positions of the beam limiting device as output data or a reference standard into the initial machine learning model for training.

It should be understood that the system and modules thereof in FIG. 2 may be implemented in various ways. For example, in some embodiments, the system and modules thereof may be implemented by hardware, software, or a combination of software and hardware. The hardware may be implemented using a dedicated logic, and the software may be stored in memory and executed by a suitable instruction execution system, such as a microprocessor or specially designed hardware. Those skilled in the art would appreciate that the methods and systems described above may be implemented using computer-executable instructions and/or control codes contained in a processor, for example, a carrier medium such as a magnetic disk, CD, or DVD-ROM, a programmable memory such as a read-only memory (firmware), or a data carrier such as an optical or electronic signal carrier. The system and modules thereof of the present disclosure may not only be implemented by a hardware circuit such as a very large scale integrated circuit or gate array, a semiconductor such as a logic chip, a transistor, etc., or a programmable hardware device such as a field programmable gate array, a programmable logic device, etc., may be implemented by software executed by various types of processors, or may be implemented by a combination (e.g., firmware) of the above hardware circuits and software.

It should be noted that the above description of the system and modules thereof is merely provided for the purposes of illustration, and not intended to limit the scope of the present disclosure. It can be understood that for those skilled in the art, after understanding the principle of the system, various modules may be combined arbitrarily, or a subsystem may be formed to connect with other modules without departing from the principle. For example, in some embodiments, the optical image information obtaining module 210, the target part information obtaining module 220, and target position information determination module 230 disclosed in FIG. 2 may be different modules in one system, or one module implementing the functions of the above two or more modules. As another example, multiple modules may share one storage module, and each module may have its own storage module. Such variations are all within the scope of the present disclosure.

In some embodiments of the present disclosure, a system for labelling an orientation of a target part may include an optical image information obtaining module and an orientation information determination module. In some embodiments, the system for labelling the orientation of the target part may further include an orientation information labelling module.

The optical image information obtaining module may be configured to obtain the optical image information of the target part of the target object.

The orientation information determination module may be configured to determine orientation information of the target part of the target object by processing the optical image information.

The orientation information labelling module may be configured to label a medical image of the target object based on the orientation information. In some embodiments, the orientation information labelling module may be further configured to obtain the medical image of the target part and label the orientation information in the medical image. In some embodiments, the orientation information labelling module may be further configured to determine protocol information based on the orientation information and label the medical image of the target part based on the protocol information.

FIG. 3 is a flowchart illustrating an exemplary process for determining information of a target position of a beam limiting device according to some embodiments of the present disclosure. Specifically, the process 300 for determining the information of the target position of the beam limiting device may be performed by the system 200. As shown in FIG. 3, the process 300 may include the following operations.

In 310, optical image information of a target object may be obtained. Specifically, the operation 310 may be performed by the optical image information obtaining module 210.

In some embodiments, the target object may be understood as an object to be irradiated, which may include a human body or other experimental bodies. The other experimental bodies may include living animals, or non-living experimental models. The optical image information may be visible light image information of the target object. For example, the optical image information may be a visible light whole-body image of the human body or other experimental bodies, or a video that can reflect the whole-body image of the human body or other experimental bodies. In some embodiments, the optical image information obtaining module 210 may obtain the optical image information of the target object through a camera device. In some embodiments, the camera device may be fixedly arranged on a medical imaging device, or at a fixed position outside the medical imaging device. The fixed position of the camera device is not specifically limited in the present disclosure, as long as the camera device can obtain the whole-body image of the target object through one or more pictures.

In 320, target part information of the target object may be obtained. Specifically, the operation 320 may be performed by the target part information obtaining module 220.

A target part may refer to an organ to be irradiated on the target object in a medical task. The target part information may refer to information that can reflect the organ to be irradiated. For example, the target part information may be a name of the organ to be irradiated. As another example, the target part information may be information of a specific position of the organ to be irradiated. In some embodiments, the target part information obtaining module 220 may obtain protocol information related to the target object and obtain the target part information of the target object based on the protocol information. The protocol information may include the target part information of the target object.

In some embodiments, the target part information obtaining module 220 may obtain a medical image of the target part of the target object. A doctor may obtain the target part of the target object based on the medical image. In some embodiments, the target part information obtaining module 220 may obtain label information of the medical image corresponding to the target object, and then determine the target part of the target object based on the label information. The medical image corresponding to the target object may include a target photographing part of the target object. The label information may be used to reflect a name of the target photographing part and an orientation of the target photographing part relative to the target object. More descriptions regarding the label information of the medical image may be found elsewhere in the present disclosure (e.g., at least part of the contents in FIGS. 4-7). In some embodiments, the target part information obtaining module 220 may obtain the target part information of the target object in any other manner. For example, the target object may inform the doctor of the target part information. In some embodiments, the medical image may be understood as a medical image collected by a medical imaging device. The medical imaging device 110 may include, but is not limited to, a DR device, a CT device, an X-ray machine, a linear accelerator, a C-arm machine, or the like.

In some embodiments, the obtaining the target part information of the target object in operation 320 may include determining the target part information of the target object by processing the optical image information of the target object. More descriptions regarding obtaining the target part information by processing the optical image information may be found elsewhere in the present disclosure (e.g., at least part of the content in FIGS. 4-7).

In 330, information of a target position of a beam limiting device may be determined. Specifically, the operation 330 may be performed by the target position information determination module 230.

In some embodiments, when performing operation 330 to determine the information of the target position of the beam limiting device, a processing device may directly determine the information of the target position of the beam limiting device by processing the optical image information and the target part information, details of which may be found in operation 336; the processing device may determine information of a position to be irradiated by processing the optical image information and the target part information, and determine the information of the target position of the beam limiting device based on the information of the position to be irradiated and information of an initial position of the beam limiting device, details of which may be found in operations 332 and 334.

In 332, the information of the position to be irradiated may be determined based on the optical image information and the target part information.

In some embodiments, the position to be irradiated may be understood as a position of a region that needs to be irradiated on the target object, and may also be referred to as a position of a region to be irradiated. The information of the position to be irradiated may refer to information capable of reflecting the position of the region to be irradiated. Specifically, in some embodiments, the information of the position to be irradiated may be position information of an organ to be irradiated of the target object on an optical image. For example, the information of the position to be irradiated may include one or more of a position of the organ to be irradiated reflected on the optical image, an area size of the organ to be irradiated reflected on the optical image, or the like.

In some embodiments, a processing device may process the optical image based on the target part information, and then output the information of the position to be irradiated corresponding to a target part. In some embodiments, when the target part information includes a medical image corresponding to the target part, the processing device may determine a position of the target part reflected on a surface of the target object on the optical image by performing an image fusion processing on the optical image and the medical image. For example, a contour of the target part may be displayed directly on the optical image. In some embodiments, in response to that the target part information is obtained from protocol information, the processing device may process and analyze the optical image to determine an approximate position of the organ of the target object on the optical image, and determine the position information of the target part reflected on the surface of the target object based on the target part in the protocol information. For example, a contour or region of the organ corresponding to the target part in the protocol information may be directly displayed on the optical image.

In some embodiments, the processing device may perform the above one or more operations using a preset algorithm. The preset algorithm may include, but is not limited to, a machine learning model, or the like. For example, the processing device may directly determine the position (i.e., the position to be irradiated) of the target part reflected on the surface of the target object using the machine learning model based on the optical image information and the target part information.

In some embodiments, the preset algorithm may be a first machine learning model. In some embodiments, when the target part information includes a medical image, the optical image of the target object and the medical image of the target part may be input into the first machine learning model, and the first machine learning model may directly output the information of the position to be irradiated. In some embodiments, the information of the position to be irradiated output by the first machine learning model may include an optical image with a position label. In some embodiments, the information of the position to be irradiated output by the first machine learning model may include coordinate information of the position to be irradiated. In some embodiments, in response to that the target part information is obtained from the protocol information, the protocol information may be processed to extract the target part information in the protocol information, and then the target part information may be subjected to feature processing, and processed feature information corresponding to the target part information and the optical image of the target object may be input into the first machine learning model, accordingly, the first machine learning model may directly output the optical image with the position label or the coordinate information of the position to be irradiated. Specifically, a training process of the first machine learning model may be described in detail hereinafter.

In 334, the information of the target position of the beam limiting device may be determined based on the information of the position to be irradiated and the information of the initial position of the beam limiting device.

The initial position of the beam limiting device may refer to a position before movement of the beam limiting device when irradiation has not started. The information of the initial position of the beam limiting device may refer to information capable of reflecting the initial position of the beam limiting device. Specifically, the information of the initial position of the beam limiting device may be understood as a distance between the beam limiting device and the target object to be irradiated before movement of the beam limiting device.

The target position of the beam limiting device may refer to a position to be reached after movement of the beam limiting device, and correspond to the information of the position to be irradiated. The information of the target position of the beam limiting device may refer to the information capable of reflecting the target position of the beam limiting device. In some embodiments, the information of the target position of the beam limiting device may include positions (e.g., spatial coordinate positions of blades after the beam limiting device reaches the target position) of the blades of the beam limiting device after the beam limiting device reaches the target position, or an opening size (e.g., positions of the blades on an end face of the beam limiting device after the beam limiting device reaches the target position) of the blades in the end face of the beam limiting device after the beam limiting device reaches the target position, etc.

In some embodiments, the information of the initial position of the beam limiting device may be obtained through protocol information related to the target object. The protocol information may include the information of the initial position of the beam limiting device. In some embodiments, the information of the initial position of the beam limiting device may be obtained in other manners. Other manners may include an automatic obtaining manner and a manual obtaining manner. The automatic obtaining manner may include that the system directly obtains measurement data from a distance detection sensor, a laser detection device, an infrared detection device, etc. The manual obtaining manner may include, but is not limited to, that a doctor manually measures the positions of the blades of the beam limiting device using an additional laser detection device, that the doctor manually measures the positions of the blades of the beam limiting device using an additional infrared detector, etc. For example, after the doctor places the laser detection device in a suitable position, the laser may emit laser signals to the beam limiting device, and then a laser receiver of the laser detection device may receive the laser signals, so that the laser detection device may determine the positions of the blades of the beam limiting device, and then the doctor may manually input the positions of the blades to the determination module 230 through an external input device. The external input device may include, but is not limited to, a mouse, a keyboard, or the like. In some embodiments, the information of the initial position of the beam limiting device may be preset in an algorithm.

In some embodiments, the determination module 230 may determine the information of the target position of the beam limiting device based on the information of the position to be irradiated and the information of the initial position of the beam limiting device. Specifically, the determination module 230 may determine a distance between the beam limiting device and the target object based on the initial position of the beam limiting device, and determine the information of the target position of the beam limiting device based on the position information of the region to be irradiated on the target object and the distance between the beam limiting device and the target object to cause a region where the rays pass through the target position of the beam limiting device and irradiate the target object may match as much as possible with the region to be irradiated.

The processing device may accurately determine the information of the position to be irradiated based on the optical image information and the target part information, and then accurately determine the information of the target position of the beam limiting device based on the information of the position to be irradiated and the information of the initial position of the beam limiting device, which is suitable for situations where the initial position of the beam limiting device often changes. In the embodiments, the position of the region to be irradiated may be determined first, and then the target position of the beam limiting device may be calculated based on the current position of the beam limiting device, which may adapt to more scenarios with different initial positions of the beam limiting device, and have higher flexibility.

In 336, the information of the target position of the beam limiting device may be determined based on the optical image information and the target part information.

The target position of the beam limiting device may be the same as the target position in operation 334, which is not repeated herein, and details thereof please refer to the description of the corresponding part in operation 334. In some embodiments, the processing device may perform the above one or more operations using a preset algorithm. The preset algorithm may include any algorithm capable of determining the information of the target position of the beam limiting device. The any algorithm may be understood as a preset instruction capable of reflecting a corresponding relationship between the optical image information and the target part information and the information of the target position of the beam limiting device. In some embodiments, the determination module 230 may input the optical image information and the target part information into the preset algorithm, and then the preset algorithm may directly output the information of the target position of the beam limiting device. In the embodiments, an initial position of the beam limiting device may be considered in advance. If the initial position changes, a corresponding adjustment may be made in the preset algorithm.

In some embodiments, the preset algorithm may include, but is not limited to, a machine learning model, or the like. In some embodiments, the preset algorithm may be a second machine learning model. The information of the target position of the beam limiting device may be determined by inputting the optical image information and the target part information into the second machine learning model. In some embodiments, in response to that the initial position of the beam limiting device during actual irradiation is consistent with the initial position during training, the determination module 230 may input the optical image information and the target part information into the second machine learning model, and the second machine learning model may output coordinate values of the target position of the beam limiting device, so as to directly determine the information of the target position of the beam limiting device.

In some embodiments, when the target part information includes a medical image, the optical image of the target object and the medical image of the target part may be input into the second machine learning model, and the second machine learning model may directly output the information of the target position of the beam limiting device. For example, the second machine learning model may directly output the coordinates of the target position of the beam limiting device. In some embodiments, in response to that the target part information is obtained from protocol information, the target part information in the protocol information may be extracted by processing the protocol information, and then the target part information may be subjected to feature processing. The processed feature information corresponding to the target part information and the optical image of the target object may be input into the second machine learning model, accordingly, the second machine learning model may directly output the information of the target position of the beam limiting device, such as coordinate information of the target position of the beam limiting device. In addition, a training process of the second machine learning model may be described in detail hereinafter.

In some embodiments, after the information of the target position of the beam limiting device is determined, the beam limiting device may be directly controlled to move to the target position based on the information of the target position information, the details thereof please see operation 360. In some embodiments, whether the target position is greater than a preset threshold range may be determined. In response to that the target position is greater than the preset threshold range, a prompt message may be sent to inform that the current beam limiting device may not meet the photographing requirements of the target position, the details thereof please see operations 340 and 350, which may prevent the beam limiting device from irradiating the target part when the beam limiting device cannot irradiate the whole target part, resulting in a photographing failure.

In some embodiments, when an area of the target part on the optical image in the information of the position to be irradiated is greater than a maximum area that can be covered by a radiation beam emitted by the beam limiting device, the beam limiting device may only obtain a local medical image of the target part in one time of photographing. In order to obtain a complete medical image of the whole target part, the photographing of the target part may be divided into at least two separate times of photographing, and then medical images obtained by the at least two separate times of photographing may be spliced together to obtain the complete medical image of the target part. In some embodiments, whether the target part needs to be spliced or how many segments it is divided into may be determined by the processing device, or according to the protocol information.

In some embodiments, when the target part needs to be divided into at least two parts for irradiation, the information of the position to be irradiated may include at least two sub-regions to be irradiated, accordingly, the information of the target position of the beam limiting device may include information of at least two sub-target positions corresponding to the at least two sub-regions to be irradiated. For example, the target part may be divided into two parts for photographing, the part of the first photographing may be an upper half part of the target part, and the part of the second photographing may be a lower half part of the target part. It is necessary to determine an upper half region to be irradiated on the target object based on the upper half part of the target part, and a lower half region to be irradiated on the target object based on the lower half part of the target part. The two regions to be irradiated may be regarded as the sub-regions to be irradiated. Two sets of information of target positions of the beam limiting device respectively determined based on the two sub-regions to be irradiated may be regarded as information of two sub-target positions.

In some embodiments, whether the photographing of the target part needs to be divided into multiple photographing or how many times the photographing needs to be divided may be determined through the protocol information. For example, the protocol information may include the target part information and two sub-target parts corresponding to the target part, accordingly, the sub-regions to be irradiated may be determined based on the sub-target parts in the protocol information. In some embodiments, the processing device may obtain the sub-regions to be irradiated corresponding to the sub-target parts by processing the optical image of the target object based on the information of the sub-target parts of the target part in the protocol information, the specific process thereof please refer to the related description of operation 332 in the present disclosure.

In some embodiments, whether the photographing of the target part needs to be divided into multiple photographing or how many times the photographing needs to be divided may be automatically determined by the processing device. For example, the processing device may automatically plan the sub-regions to be irradiated corresponding to the target parts based on image information and the target part information.

In some embodiments, after the sub-regions to be irradiated are determined, information of each of target positions corresponding to each sub-region to be irradiated may be determined based on information of an output position of the beam limiting device. The information of the target position may be regarded as information of the target sub-position. More descriptions regarding determining the target positions of the beam limiting device based on the regions to be irradiated may be found elsewhere in the present disclosure.

In 340, whether the information of the target location is greater than a preset threshold range may be determined.

The preset threshold range may refer to a range of a target part that can be covered by a radiation beam emitted by the beam limiting device. In some embodiments, the preset threshold range may be stored in the storage device 150. In some embodiments, the preset threshold range may be obtained according to the doctor's previous experience. In some embodiments, the preset threshold range may be set according to sign information of the target object. For example, for target objects whose heights or body widths are within a certain range, the threshold range corresponding to the target objects may be a first group. For target objects whose heights (or body widths, etc.) are within other ranges, the threshold range corresponding to the target objects may be a second group. In some embodiments, a threshold range corresponding to the sign information of the target object may be obtained by searching a target part database of the beam limiting device based on the sign information of the target object and used as the preset threshold range.

In some embodiments, when the determination system 200 determines that the information of the target position is less than or equal to the preset threshold range, the determination system 200 may perform operation 360. When the determination system 200 determines that the information of the target position is greater than the preset threshold range, the determination system 200 may perform operation 350.

In 350, a prompt message may be sent.

When the information of the target position exceeds the preset threshold range, the processing device may send the prompt message to inform a medical personnel that the current beam limiting device cannot reach the target position determined by the system. In such cases, the medical personnel may pause the photographing, and adjust the beam limiting device based on recorded information in the prompt message. In some embodiments, the prompt message may include whether the information of the target position exceeds the preset threshold range, how much the information of the target position exceeds the preset threshold range, and the specific content of the information of the target position, which may be used as a reference for subsequent adjustment of the beam limiting device. Specifically, the prompt message may include one or more of a text prompt, a voice prompt, a video prompt, a light prompt, or the like. For example, when the determination system 200 determines that the information of the target position is greater than the preset threshold range, the determination system 200 may send an alarm sound. Through the setting of the prompt message, the doctor may quickly find out the problem, stop the follow-up photographing operation in time, and adjust the beam limiting device based on the recorded information in the prompt message, thereby improving work efficiency.

In 360, movement of the beam limiting device may be controlled based on the information of the target position of the beam limiting device.

In some embodiments, the determination system 200 may control the movement of the beam limiting device based on the information of the target position. For example, the determination system 200 may control the beam limiting device to move from the initial position to the position to be irradiated based on the coordinate values of the target position of the beam limiting device. As another example, after the beam limiting device moves to the target position, the control system 200 may control the blades to be at an opening position of the end face of the beam limiting device, so that a region where the rays pass through the target position of the beam limiting device and irradiate the target object may match as much as possible with the region to be irradiated.

In some embodiments, the determination system 200 may obtain the first machine learning model by the following operations. The determination system 200 may obtain an initial machine learning model. In some embodiments, the determination system 200 may obtain the initial machine learning model from the storage device 150 through the network 120. The initial machine learning model may include one or any combination of a DNN model, a CNN model, an RNN model, an LSTM network model, etc. The determination system 200 may obtain initial sample training data. In some embodiments, the determination system 200 may obtain the initial sample training data from the storage device 150 through the network 120. In some embodiments, the initial sample training data may include historical optical images of historical target objects and historical medical images of one or more target parts of the historical target objects. The historical optical images may refer to photographed visible light images of the historical target objects. The historical medical images may refer to medical images corresponding to one or more target organs of the historical target objects photographed by a medical imaging device. The medical imaging device may include, but is not limited to, a DR device, a CT device, an X-ray machine, a linear accelerator, or a C-arm machine. For example, the historical medical images may be images obtained by photographing the target part by the CT device.

In some embodiments, the determination system 200 may determine label information of the historical optical images based on fusion result information of the historical optical images and the historical medical images. In some embodiments, the fusion result information may refer to corresponding relationships between the positions of the target parts of the historical optical images and the positions of the target parts of the historical medical images. For example, a historical medical image may be an X-ray image of the lungs, a historical optical image may be a visible light image of the whole body of the target object, and fusion result information of the historical medical image and historical optical image may be a position, on the historical optical image, of a target part corresponding to the historical optical image. The label information may include position information of the target parts in the historical optical images. The determination system 200 may input the historical optical images and the historical medical images as input data and the label information as output data into the initial machine learning model for training to obtain a trained first machine learning model.

In some embodiments, the determination system 200 may obtain the second machine learning model by the following operations. The determination system 200 may obtain an initial machine learning model. In some embodiments, the determination system 200 may obtain the initial machine learning model from the storage device 150 through the network 120. The initial machine learning model may include one or any combination of a DNN model, a CNN model, an RNN model, an LSTM network model, etc. The determination system 200 may obtain initial sample training data. In some embodiments, the determination system 200 may obtain the initial sample training data from the storage device 150 through the network 120. In some embodiments, the initial sample training data may include historical optical images of historical target objects and historical medical images of one or more target parts of the historical target objects.

In some embodiments, the determination system 200 may determine information of historical target positions of the beam limiting device based on fusion result information of the historical optical images and the historical medical images. The historical target positions may refer to target positions of the beam limiting device corresponding to historical regions to be irradiated. The historical regions to be irradiated may be determined based on fusion results of the historical optical images and the historical medical images. Specifically, the determination system 200 may obtain the target part information based on the historical medical images, label the target part information on the corresponding positions of the historical optical images to obtain historical regions to be irradiated on the historical target objects, and then determine the information of the historical target positions of the beam limiting device based on the historical regions to be irradiated on the historical target objects.

In some embodiments, the determination system 200 may input the historical optical images and the historical medical images as input data and the information of the historical target positions of the beam limiting device as output data into the initial machine learning model for training to obtain a trained second machine learning model.

Further, in some embodiments, an initial position of the beam limiting device may be considered during the training process of the second machine learning model. For example, after the historical regions to be irradiated are determined, the information of the historical target positions of the beam limiting device may be determined based on the initial position of the beam limiting device, accordingly, the historical optical images, the initial position of the beam limiting device, and the historical medical images may be input as the input data into the initial machine learning model for training.

In some embodiments, the determination system 200 may obtain the first machine learning model or the second machine learning model by the following operations. The determination system 200 may obtain an initial machine learning model. In some embodiments, the determination system 200 may obtain the initial machine learning model from the storage device 150 through the network 120. The initial machine learning model may include one or any combination of a DNN model, a NN model, an RNN model, an LSTM network model, etc. The determination system 200 may obtain initial sample training data. In some embodiments, the determination system 200 may obtain the initial sample training data from the storage device 150 through the network 120. In some embodiments, the initial sample training data may include historical optical images of historical target objects, age information of the historical target objects, and historical medical images of one or more target parts of the historical target objects. The determination system 200 may determine label information of the historical optical images based on fusion result information of the historical optical images, the age information of the target objects, and the historical medical images. In some embodiments, the label information may include position information of the target parts in the historical optical images or information of historical target positions of the beam limiting device. The system 200 may input the historical optical images, the age information of the target objects, and the historical medical images as input data and the label information as output data or a reference standard into the initial machine learning model for training. The label information may be label information of the historical optical images. The target parts in the historical medical images and the age information of the target objects may be labelled on the label information of the historical images. The age information of the target objects is introduced into the training data of the model, which reflects the influence of age on the information of the target position of the beam limiting device, so as to better protect children from radiation harm.

It should be noted that the above descriptions of the process 300 are merely provided for the purposes of example and illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 4:
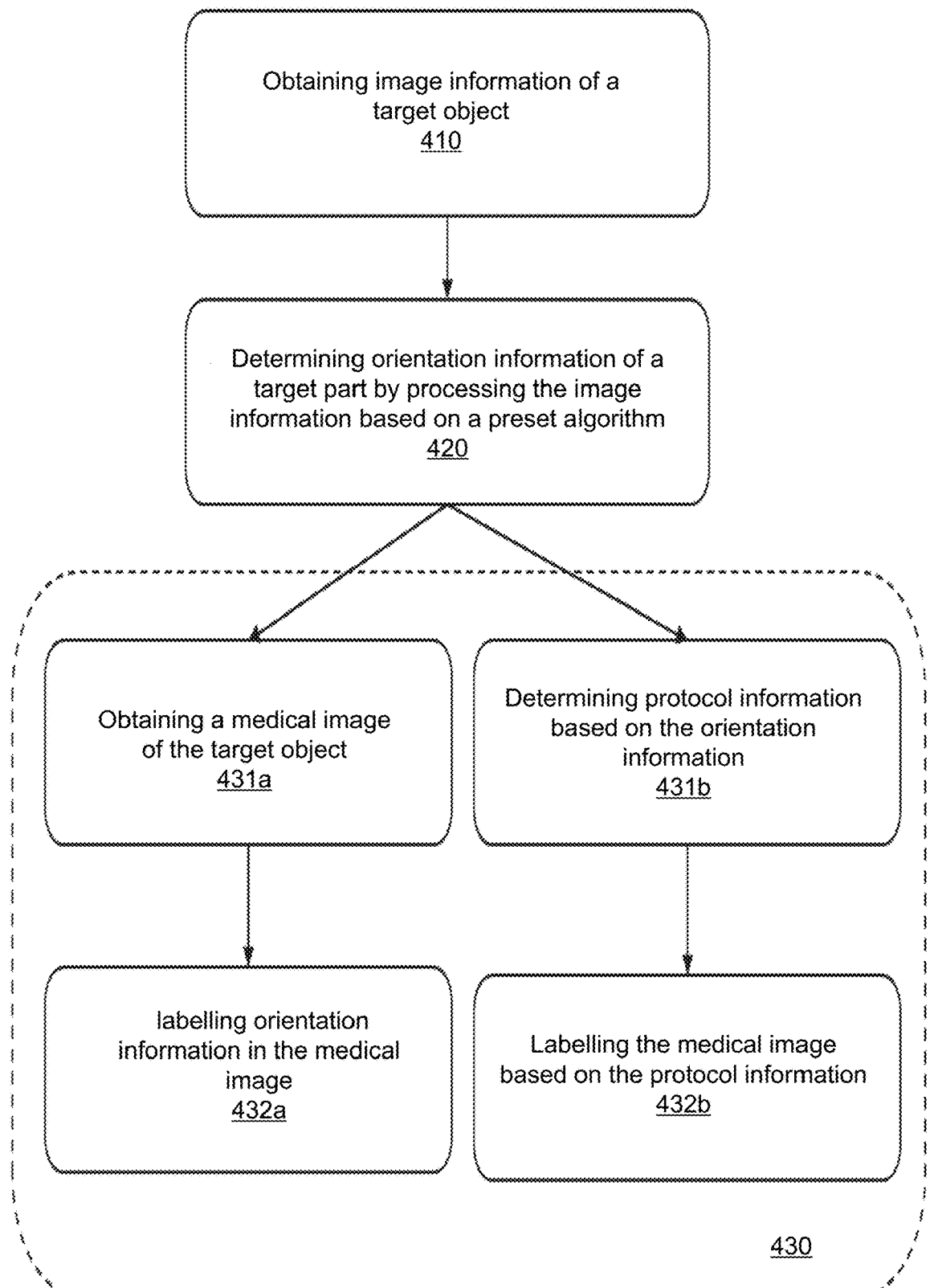
FIG. 4 is a flowchart illustrating an exemplary process for labelling a target orientation according to some embodiments of the present disclosure.

FIG. 4 is a flowchart illustrating an exemplary process for labelling a target orientation according to some embodiments of the present disclosure.

In some embodiments, the process 400 may be performed by an orientation labelling system of a target part. The process 400 may include the following operations.

In 410, image information of a target object may be obtained. In some embodiments, operation 410 may be performed by an image information obtaining module.

The target object may include an object for which a medical image is to be taken, such as a patient. The image information of the target object may include image information of a target part of the target object.

The image information may refer to an image of the target object (e.g., the human body and various parts or organs of the human body) obtained by a camera device. In some embodiments, the image may include a still image or a video image of the target object. In some embodiments, the still image may include a stationary image such as a photograph, a picture, or the like. In some embodiments, the video image may refer to a dynamic image, which may include but is not limited to a video, an animation, or the like. In some embodiments, a video stream may be derived from the video image. The video stream may include multiple frames of still images. In some embodiments, the image may be an optical image (including a visible light image and a non-visible light image) or a non-optical image, accordingly, the image information may include optical image information or non-optical image information. In some embodiments, the camera device may be an optical device, such as a camera or other image sensors. In some embodiments, the camera device 160 may be a non-optical device, which may obtain a heat map capable of reflecting features such as a shape and a size of the target object based on collected distance data.

In some embodiments, the camera device 160 may include any device with a two-dimensional or three-dimensional image capture function. In some embodiments, the image information may at least include positioning information of the target part of the target object relative to the medical imaging device 110. A processor may determine the target part based on the positioning information. In some embodiments, the positioning information may include whether there is an object to be irradiated in a radiation irradiation region of the medical imaging device, or whether there is an object to be irradiated on a placement platform (e.g., a hospital bed) of the medical imaging device. The placement platform or the radiation irradiation region may be regarded as a positionable region. The object to be irradiated in the positionable region may be regarded as a target part of the target object.

In some embodiments, the medical imaging device 110 may be adjusted based on the image information of the target part, so that the target part may be in a ray path of a ray source. In some embodiments, the operation of adjusting the medical imaging device 110 may be performed manually or automatically by a machine. In some embodiments, the operation of adjusting the medical imaging device may include adjusting the ray source of the medical imaging device 110, adjusting a detector of the medical imaging device 110, or adjusting the detector and the ray source, as long as the adjustment may make the target part in the ray path of the ray source.

In some embodiments, in the process of adjusting the posture and/or position of the target part of the target object to make the target part in the ray path of the ray source of the medical imaging device, the target part in the positionable region may be determined.

In some embodiments, in the process of manually or automatically adjusting the movement of the ray source of the medical imaging device 110 to align with the target part, the target part may be determined. For example, in response to that the patient has entered a region to be photographed by the medical imaging device 110 for positioning, and the target part is located on a left side of the ray source of the medical imaging device 110, the target part may be adjusted to move to a right side to make the target part in the ray path of the ray source of the medical imaging device 110, or t the ray source of the medical imaging device 110 may be adjusted to move to the left side to make the target part in the ray path of the ray source of the medical imaging device 110. During the above process, the processor may determine the target part in the positionable region based on the collected image information (e.g., video information corresponding to the process).

The image information obtaining module may obtain the image information captured by the camera device 160 via wire or wireless, and further recognize the target object in the image information. In some embodiments, the system may export a video stream from the input video images to process frame by frame. In some embodiments, the processing may include filtering and denoising the image, normalizing the grayscale of the image, horizontally rotating the image, correcting the scale of the image, or the like. In some embodiments, the processing may include recognizing or segmenting the target object or the target part in the image.

In 420, orientation information of the target part may be determined by processing the image information. In some embodiments, operation 420 may be performed by an orientation information determination module.

In some embodiments, the target part may include all or a part of tissue or organs of the target object. For example, the target part may include left ankle, chest, or the like.

In some embodiments, the orientation information of the target part may include at least one of a left-right orientation, an up-down orientation, and a front-rear orientation of the target part relative to the target object. In some embodiments, the orientation information of the target part relative to the target object may include left-right orientation information, such as left knee joint. In some embodiments, the orientation information of the target part relative to the target object may include up-down information, such as upper spine. In some embodiments, the orientation information of the target part relative to the target object may include front-rear orientation information, such as back. In some embodiments, the orientation information of the target part relative to the target object may be left, right, up, and down information, for example, the target part may be upper left hip joint.

In some embodiments, the orientation information of the target part may include a ray incident orientation of the medical imaging device, or the like. The ray incident orientation of the medical imaging device may include a positional relationship between an initial incident direction of the rays and the target object or the target part. For example, when the target part for which a medical image is photographed is the left hand, the orientation information may include the hand on the left side of the body and whether the back of the hand faces the initial incident direction of the rays or the palm faces the initial incident direction of the rays. As another example, when the target part for which a medical image needs to be taken on a DR scanner is the left thigh, the orientation information may include the thigh on the left side of the body and whether the face of the target object faces the initial incident direction of the rays or the back of the target object faces the initial incident direction of the rays, i.e., whether the patient is lying flat on a scanning bed facing the initial incident direction of the rays or lying flat on the scanning bed with the back facing the initial incident direction of the rays.

In some embodiments, the orientation information determination module may receive the image information containing the target part of the target object through the network, recognize the image of the target part based on a preset algorithm, and determine the orientation information of the target part by processing the image information. For example, during the continuous process of photographing the video image, the camera device photographs all the images from the process of patient positioning to the exposure of the patient. During the above process, the ray source and/or placement platform and/or camera may be configured to be movable. The orientation information determination module may automatically recognize the orientation information of the target part. For example, during the process of taking X-rays of the left knee joint through DR, the camera device photographs that the medical imaging equipment moves the ray source above the left knee joint, and the orientation information determination module may analyze and recognize that the target part is the left knee joint in real time.

In some embodiments, the preset algorithm may include an algorithm for processing and analyzing an image. Specifically, the preset algorithm may first perform a processing such as an image segmentation on the image information of the target object obtained by the camera device to determine the target part in the image information at a positioning position based on the positional relationship between the target part in the image information and the medical imaging device, and then analyze and determine the orientation information of the target part relative to the target object.

In some embodiments, the preset algorithm may include an image matching algorithm. Specifically, a matching degree between the image information of the target object obtained by the camera device and the image information in an associated database may be calculated based on the image matching algorithm. The image information with a highest matching degree may be selected as the obtained image information to be further analyzed to determine the orientation information of the target part relative to the target object. In some embodiments, the image matching algorithm may include a grayscale-based image matching algorithm and a feature-based image matching algorithm.

In some embodiments, the preset algorithm may also include a machine learning model. Specifically, the image information of the target object obtained by the camera device may be input into a trained machine learning model, and the orientation information of the target part may be determined based on output data of the trained machine learning model. In some embodiments, the output data of the trained machine learning model may include a name of the target part and corresponding orientation information thereof, such as the left knee joint. In some embodiments, the image information obtained by the camera device may be preprocessed to screen out images with higher quality, which may be images with higher definition, or images including the whole target object and in which the target part in the placement position. The screened images may be input into the trained machine learning model. The trained machine learning model may automatically output the orientation information of the target part relative to the target object based on the input.

In some embodiments, the machine learning model may include a deep neural network (DNN), such as a convolutional neural network (CNN), a deep belief network (DBN), a stochastic Boolean neural network (RBN), etc. The deep learning model may include multi-layer neural network structures. Taking the convolutional neural network as an example, the convolutional neural network may include an input layer, a convolutional layer, a dimensionality reduction layer, a hidden layer, an output layer, etc. The convolutional neural network may include one or more convolution kernels for convolution operations.

In some embodiments, the trained machine learning model may be obtained by training an initial machine learning model using training sample data. The training sample data may include historical images of target objects. The historical images may include images of target parts. The target parts and orientation information thereof in the historical images may be labelled. For example, the label information of a target part may include the left knee joint. The trained machine learning model may be obtained by inputting historical image information as the input data and the label information of the orientation information as the output data or a criterion standard into the initial machine learning model for training.

In 430, a medical image of the target object may be labelled based on the orientation information.

The system may obtain the medical image of the target object through the medical imaging device. An orientation information labelling module may label the orientation information on the obtained medical image. In some embodiments, the medical image of the target object may include the medical image corresponding to the target part on the target object. In some embodiments, the medical image of the target object may include a medical image corresponding to a non-target part on the target object. The non-target part may be understood as a part that has a certain relationship with the target part. For example, if the target part is the palm, the non-target part may be the arm corresponding to the palm, and the orientation information of the palm of the target object may be labelled on the medical image of the arm of the target object.

In some embodiments, the medical image may be understood as an image obtained by a medical imaging device. In some embodiments, the medical imaging device may include a DR imaging device, a CT scanner, an MRI scanner, a B imaging scanner, a TTM scanning device, a SPECT device, or a PET scanner, accordingly, in some embodiments, the medical image may include at least one of an MRI image, an XR image, a PET image, a SPECT image, a CT image, or an ultrasound image. In some embodiments, the medical image information may include a fusion image of the above-mentioned one or more medical images. In some embodiments, the image information and the medical image may be obtained simultaneously or sequentially.

In some embodiments, the label may be a color label, a text label, or a graphic label, more specifically, for example, one of or a combination of a Chinese character label, an English label, or a graphic label. In some embodiments, each medical image may include one or more labels. For example, an R may be labelled on the photographed medical image of the right knee joint. Optionally, each medical image may include one or more labels related to the part.

In some embodiments, the label may be manually adjusted. In some embodiments, the manual adjustment may include adding one or more labels, deleting one or more labels, changing positions of one or more labels, or the like.

In some embodiments, the orientation information labelling module may directly label the target part in the medical image based on the orientation information of the target part, detailed description thereof please refer to operations 431a and 432a hereinafter. In some other embodiments, the orientation information labelling module may select a scanning protocol based on the orientation information of the target part to obtain the medical image and further label the medical image, detailed description thereof please refer to operations 431b and 432b hereinafter.

In 431a, the medical image of the target object may be obtained.

In some embodiments, the medical image may be understood as an image obtained by a medical imaging device. In some embodiments, the medical image may include an MRI image, a CT image, a cone-beam CT image, a PET image, a functional MRI image, an X-ray image, a fluoroscopy image, an ultrasound image, a SPECT image, or the like, or any combination thereof. The medical image may reflect information of a part of a patient's tissue, organ and/or bone. In some embodiments, the medical image may be one or a set of two-dimensional images, for example, a black and white X-ray film, a CT two-dimensional scanning image, etc. In some embodiments, the medical image may be a three-dimensional image, for example, a three-dimensional organ image reconstructed from different CT scan images or a three-dimensional space image output by a device capable of three-dimensional imaging. In some embodiments, the medical image may be a dynamic image within a time period, for example, a video reflecting the changes of the heart and its surrounding tissues during a cardiac cycle, etc. In some embodiments, the medical image may come from the medical imaging device, a storage module, or user input through an interactive device.

In some embodiments, the medical imaging device may obtain the medical image of the target part based on the obtained orientation information, and label the orientation information in the obtained medical image.

In 432a, the orientation information may be labelled in the medical image.

Figure 6:
FIG. 6 is a schematic diagram illustrating a medical image according to some embodiments of the present disclosure.
Figure 7:
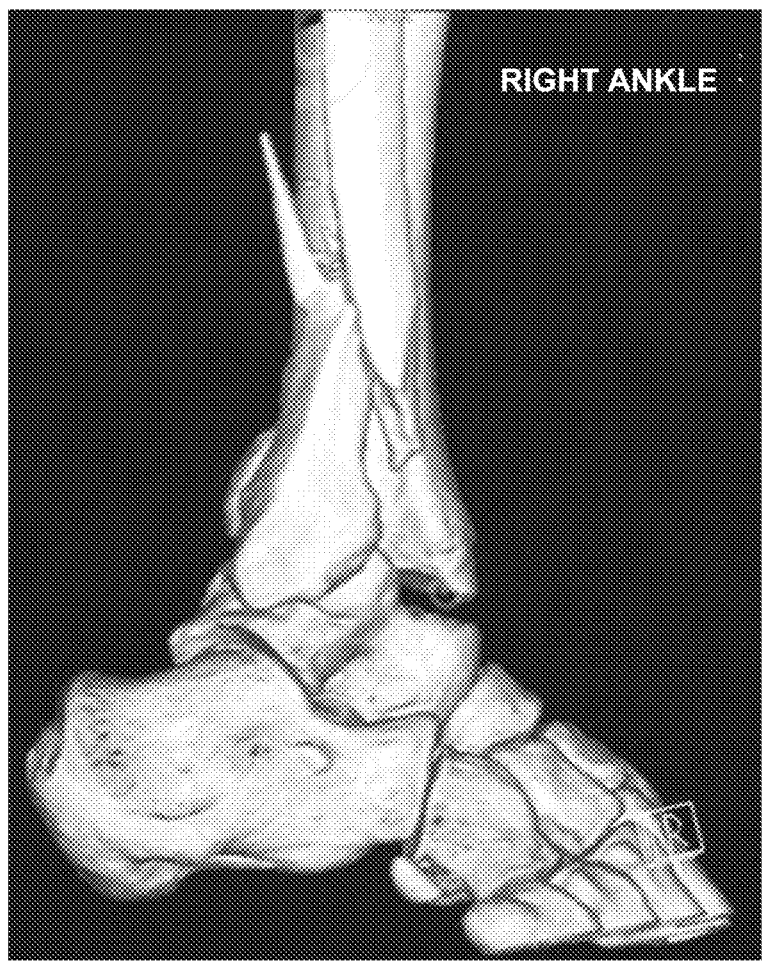
FIG. 7 is a schematic diagram illustrating a medical image according to some embodiments of the present disclosure.

In some embodiments, the orientation information may be labelled at a certain position in the medical image, for example, the orientation information may be labelled at the upper left corner of the medical image. Labelling the orientation information in the medical image may be understood as directly labelling the medical image in a displayable manner, for example, covering a certain local region of the medical image, as another example, a description may be added to the medical image to display the orientation information of the target part in the medical image. In order not to affect the doctor's observation of the target part, the position of the label may be generally set at a peripheral position of the medical image. In some embodiments, the labelled content may only include the orientation information of the target part. The doctor may determine the name of the target part through the medical image. For example, the labelled content may be the right side or may be represented by the English letter R (as shown in FIG. 6). In some embodiments, the labelled content may include the name of the target part and the orientation information thereof, for example, the labelled content may be the right ankle or may be represented by the English letter RIGHT ANKLE (as shown in FIG. 7).

In 431b, corresponding protocol information may be determined based on the orientation information.

In some embodiments, the system may select a corresponding protocol based on the orientation information of the target part, and then scan the target part of the object based on the protocol to obtain the medical image of the target part photographed by the medical imaging device. In some embodiments, the protocol may refer to a combination of photographing parameters of the medical imaging device. A corresponding protocol may be selected for the photographed target part of the patient. For example, when the left knee or chest is photographed in DR, the left knee or chest protocol may be selected during scanning.

In 432b, the medical image may be labelled based on the protocol information.

In some embodiments, the system may further label the medical image based on the selected protocol. In some embodiments, the system may detect the used protocol, and further label the orientation information in the used protocol on the medical image or its perspective content.

In some embodiments, the label of the labelled medical images may be adjusted. The adjustment may include manual adjustment and automatic machine adjustment. For example, when finding that at least one of the labelled content, the labelled position, and the labelled manner of the label information on the medical image is inappropriate, the doctor may manually adjust the medical image. As another example, the machine may automatically check the label information on the medical image, and automatically adjusts the inappropriateness of the label information to ensure the accuracy of the label information.

It should be noted that the above descriptions of the flowchart are merely provided for the convenience of description, and not intended to limit the present disclosure to the scope of the illustrated embodiments. It can be understood that for those skilled in the art, after understanding the principle of the system, various amendments and modifications in the form and details of the application field in which the methods and systems are implemented may be made without departing from the principle. However, these amendments and modifications are still within the scope of the above descriptions. For example, the system may directly recognize the target part without recognizing the target object. For example, in some embodiments, the flowchart illustrating the exemplary process for labelling the orientation of the target part may further include obtaining optical image information of the target object; determining the target part information of the target object, the target part information including the orientation information of the target part, and determining the label information of the medical image based on the orientation information of the target part. In some embodiments, the flowchart illustrating the exemplary process for labelling the orientation of the target part may further include labelling the medical image of the target object based on the orientation information of the target part information.

Figure 5:
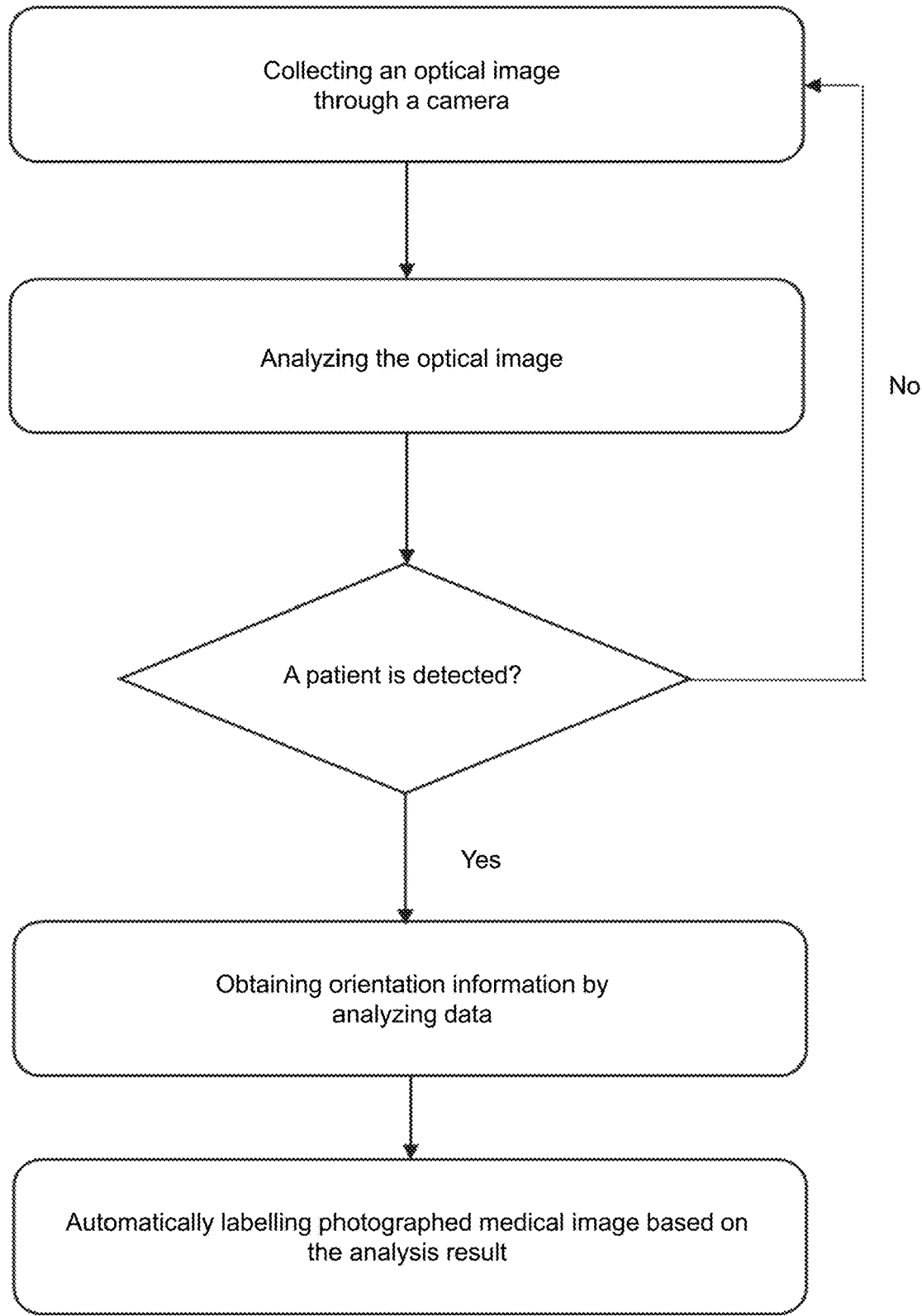
FIG. 5 is a flowchart illustrating an exemplary process for labelling a target orientation according to some embodiments of the present disclosure.

FIG. 5 is a flowchart illustrating an exemplary process for labelling a target orientation according to some embodiments of the present disclosure. A camera device may include a camera. An image obtained by the camera may be optical image information.

The process may be performed by a system for labelling an orientation of a target part. The system may obtain a medical image of the target part using a medical imaging device, and label generated orientation information of the target part in the medical image. In some embodiments, the system may include a camera device configured to obtain optical image information of a target object. The system may include the medical imaging device configured to obtain the medical image of the target part of the target object. The system may include an information processing device configured to determine orientation information of the target part by processing the optical image information based on a preset algorithm and label the orientation information in the medical image.

In some embodiments, the target object may be positioned first, and then the camera device may start to collect the optical image information. An image information obtaining module may analyze the collected optical image information and determine whether a patient is detected in the image collected by the camera device. In some embodiments, whether the patient is detected may refer to whether the collected image contains the patient and the target part of the patient is within a positionable region.

When the camera device can clearly photograph the patient and the target part is within the positionable region, the positioning of the target object may be completed and the patient may be detected. For example, taking a CT scanner as an example, the target object (e.g., the patient) may first enter the medical imaging device for positioning, that is the patient may be placed on a scanning bed of the CT scanner, and a posture and/or position of the patient on the scanning bed and a position of the scanning bed may be adjusted, so that a radiation beam of the CT scanner may partially or completely pass through the target part of the target object. During the positioning process and/or after the positioning and before the scanning bed is moved into the medical imaging device and/or during the process of the scanning bed is moved into the medical imaging device and/or a positioning image of the patient is scanned, the camera device may obtain the optical image information simultaneously, and the image information obtaining module may analyze the obtained optical image information. If the optical image information includes the patient and the target part is in the positionable region, the positioning of the patient may be completed.

If the patient cannot be detected in the optical image information collected by the camera device 160, or the target part of the patient is not within the positionable region, it is necessary to adjust the posture or position of the patient and/or the position of the scanning table again to obtain new optical image information until the image information obtaining module determines that the optical image information includes the patient and the target part of the target object is in the positionable region, that is, the positioning of the patient is completed. For example, taking a mammography machine as an example, the patient stands in front of the mammography machine, and the breasts of the patient may be pressed between a detector housing and a compressor of the mammography machine, so that the radiation beam of the mammography machine may partially or completely pass through the breasts. The camera device may obtain the optical image of the above process simultaneously. The image information obtaining module may analyze the obtained optical image information. If the optical image information includes the patient, the positioning of the patient may be completed at this time.

In some embodiments, after the positioning is completed, the information processing device may analyze the data to obtain the orientation information, and the system may automatically label the photographed medical image based on an analysis result.

In some embodiments, the camera device may be fixedly or movably arranged on the medical imaging device. In some embodiments, the camera device may be independently arranged outside the medical imaging device. In such cases, the camera device may be fixed or movable during the process of image collection. In some embodiments, the camera device may be located on or integrated into a movable part of the medical imaging device. For example, the camera device may be located on a C-arm or a rack of the mammography machine. As another example, a rail may be fixed on the rack, and the camera device may move on the rail. After the positioning of the patient is completed, the orientation information determination module may analyze the optical image information based on a preset algorithm (e.g., a machine learning model) to obtain the target part, and further analyze to generate the orientation information of the target part.

In some embodiments, the camera device and the medical imaging device may be in data connection through a wired or wireless manner. In some embodiments, the camera device may be a camera.

The possible beneficial effects of the embodiments of the present disclosure may include but are not limited to: (1) the method can determine information of the reasonable target position of the beam limiting device based on the optical image information and target part information of the target object, so that the region where the rays pass through the target position of the beam limiting device and irradiate the target object may match as much as possible with the region to be irradiated, thereby avoiding damage of unnecessary radiation dose to the target object while ensuring the quality of imaging/treatment, accordingly, the method is very suitable for use when children are exposed to radiation to protect the children from radiation harm; (2) the beam limiting device can be controlled to move quickly to a specific position based on the determined information of the target position of the beam limiting device, thereby improving the work efficiency; (3) the position to be irradiated corresponding to the target part can be determined based on the optical image information and target part information of the target object; (4) the optical image information is processed and analyzed to obtain the orientation information of the target part based on the preset algorithm, which improves the accuracy of the orientation information recognition; (5) the orientation information of the target part can be automatically recognized using the machine, and the labelling can be performed based on the recognized orientation information, thereby improving the accuracy of the labelling; and (6) the target part in the medical image can be automatically recognized and labelled using the machine, thereby implementing automation and intelligence and improving the operation efficiency. It should be noted that different embodiments may have different beneficial effects. In different embodiments, the possible beneficial effects may be any one or a combination of the above, or any other possible beneficial effects.

Having thus described the basic concepts, it may be rather apparent to those skilled in the art after reading this detailed disclosure that the foregoing detailed disclosure is intended to be presented by way of example only and is not limiting.

Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for determining parameters related to a medical operation, comprising:
    obtaining optical image information of a target object;
    obtaining target part information of the target object; and
    determining the parameters related to the medical operation at least based on the optical image information and the target part information.

2. The method of claim 1, wherein the obtaining the target part information of the target object includes determining the target part information of the target object by processing the optical image information.

3. The method of claim 1, wherein
    the parameters related to the medical operation include information of a position to be irradiated on the target object and/or information of a target position of a beam limiting device, and
    the determining the parameters related to the medical operation at least based on the optical image information and the target part information includes:
        determining the information of the position to be irradiated on the target object and/or the information of the target position of the beam limiting device at least based on the optical image information and the target part information.

4. The method of claim 3, wherein
    the obtaining the target part information of the target object further includes obtaining protocol information related to the target object, the protocol information at least including the target part information of the target object, and
    the determining the information of the position to be irradiated on the target object and/or the information of the target position of the beam limiting device at least based on the optical image information and the target part information includes:
        determining the information of the position to be irradiated on the target object and/or the information of the target position of the beam limiting device at least based on the optical image information and the protocol information.

5. The method of claim 3, further including:
    obtaining information of an initial position of the beam limiting device; and
    in response to determining the information of the position to be irradiated on the target object based on the optical image information and the target part information, the method further includes:
        determining the information of the target position of the beam limiting device based on the information of the position to be irradiated and the information of the initial position.

6. The method of claim 3, wherein the determining the information of the position to be irradiated on the target object based on the optical image information and the target part information includes:
    determining the information of the position to be irradiated by inputting the optical image information and the target part information into a first machine learning model.

7. The method of claim 3, wherein the determining the information of the target position of the beam limiting device based on the optical image information and the target part information includes:
- determining the information of the target position of the beam limiting device by inputting the optical image information and the target part information into a second machine learning model.

8. The method of claim 1, further including:
- in response to that the information of the target position is greater than a preset threshold range, sending a prompt message.

9. The method of claim 3, wherein
- the information of the position to be irradiated includes at least two sub-regions to be irradiated, and
- the information of the target position of the beam limiting device includes information of at least two sub-target positions corresponding to the at least two sub-regions to be irradiated.

10. The method of claim 9, wherein
- the protocol information related to the target object includes at least two sub-target parts, and
- the at least two sub-regions to be irradiated are determined based on the at least two sub-target parts in the protocol information.

11. The method of claim 9, wherein
- the at least two sub-regions to be irradiated are determined by a preset algorithm, and
- the information of the at least two sub-target positions of the beam limiting device is determined based on the at least two sub-regions to be irradiated.

12. The method of claim 1, wherein
- the parameters related to the medical operation include label information of a medical image corresponding to the target object,
- the target part information includes orientation information of the target part, and
- the determining the parameters related to the medical operation at least based on the optical image information and the target part information includes:
  - determining the label information of the medical image based on the orientation information of the target part.

13. The method of claim 12, further including:
- labelling the medical image of the target object based on the orientation information of the target part.

14. The method of claim 13, wherein the labelling the medical image of the target object based on the orientation information of the target part includes:
- determining protocol information based on the orientation information; and
- labelling the medical image of the target object based on the protocol information.

15. The method of claim 12, wherein the orientation information includes at least one of a left-right orientation, a front-rear orientation, or an up-down orientation of the target part relative to the target object.

16. The method of claim 12, wherein
- in response to that the orientation information of the target part is obtained by processing the optical image information, the optical image information is processed through a preset algorithm, the preset algorithm including a machine learning model, and
- the determining the orientation information of the target part of the target object by processing the optical image information includes:
  - inputting the optical image information into the machine learning model; and
  - determining the orientation information of the target part based on output data of the machine learning model.

17. The method of claim 12, wherein
- the optical image information is obtained by a camera, and
- the medical image is one of or a fusion image of at least two of an MRI image, an XR image, a PET image, a SPECT image, a CT image, or an ultrasound image.

18. The method of claim 12, further including:
- automatically adjusting a ray source of a medical imaging device based on the optical image information of the target part, so that the target part is in a ray path of the ray source.

19. The method of claim 13, wherein the labelling the medical image of the target object based on the orientation information includes color labelling, text labelling, or graphic labelling.

20. A system for determining parameters related to a medical operation, wherein the system comprises an optical image information obtaining module, a target part information determination module, and a medical operation parameter determination module;
- the optical image information obtaining module is configured to obtain optical image information of a target object;
- the target part information determination module is configured to obtain target part information of the target object; and
- the medical operation parameter determination module is configured to determine the parameters related to the medical operation at least based on the optical image information and the target part information.

* * * * *